(12) United States Patent
Ebisawa

(10) Patent No.: US 10,499,808 B2
(45) Date of Patent: Dec. 10, 2019

(54) PUPIL DETECTION SYSTEM, GAZE DETECTION SYSTEM, PUPIL DETECTION METHOD, AND PUPIL DETECTION PROGRAM

(71) Applicant: NATIONAL UNIVERSITY CORPORATION SHIZUOKA UNIVERSITY, Shizuoka-shi, Shizuoka (JP)

(72) Inventor: Yoshinobu Ebisawa, Hamamatsu (JP)

(73) Assignee: NATIONAL UNIVERSITY CORPORATION SHIZUOKA UNIVERSITY (JP)

( * ) Notice: Subject to any disclaimer, the term of this patent is extended or adjusted under 35 U.S.C. 154(b) by 270 days.

(21) Appl. No.: 15/316,971

(22) PCT Filed: May 12, 2015

(86) PCT No.: PCT/JP2015/063586
§ 371 (c)(1),
(2) Date: Dec. 7, 2016

(87) PCT Pub. No.: WO2015/190204
PCT Pub. Date: Dec. 17, 2015

(65) Prior Publication Data
US 2017/0105619 A1    Apr. 20, 2017

(30) Foreign Application Priority Data
Jun. 9, 2014   (JP) .................................. 2014-118846

(51) Int. Cl.
*A61B 3/14*   (2006.01)
*A61B 3/10*   (2006.01)
(Continued)

(52) U.S. Cl.
CPC ............ *A61B 3/113* (2013.01); *A61B 3/0025* (2013.01); *A61B 3/11* (2013.01); *A61B 3/14* (2013.01); *G06K 9/00604* (2013.01)

(58) Field of Classification Search
CPC ................. G06T 7/0075; G06T 7/0044; G06T 2207/30201; G06T 2207/10012;
(Continued)

(56) References Cited

U.S. PATENT DOCUMENTS

| | | | | |
|---|---|---|---|---|
| 2007/0279590 | A1 | 12/2007 | Ebisawa | ........................ 351/208 |
| 2013/0329957 | A1* | 12/2013 | Ebisawa | ................. A61B 3/113 |
| | | | | 382/103 |
| 2015/0287206 | A1* | 10/2015 | Ebisawa | ................. A61B 3/111 |
| | | | | 382/154 |

FOREIGN PATENT DOCUMENTS

| | | |
|---|---|---|
| EP | 2 604 180 A1 | 6/2013 |
| JP | H06-125874 A | 5/1994 |

(Continued)

OTHER PUBLICATIONS

PCT/IB/338 Notification of Transmittal of Translation of the International Preliminary Report on Patentability including PCT/IB/373 and PCT/ISA/237 (in English) for International Application No. PCT/JP2015/063586 dated Dec. 22, 2016.
(Continued)

*Primary Examiner* — Dawayne Pinkney
(74) *Attorney, Agent, or Firm* — Ostrolenk Faber LLP

(57) ABSTRACT

A pupil detection system according to an embodiment includes a vector calculation unit configured to calculate a plurality of candidate vectors each connecting a corneal sphere center and a pupil center by a stereo method based on a first pupil image of a subject which is picked up by a first camera and a second pupil image of the subject which is picked up by a second camera, and a determination unit configured to select, from among the plurality of candidate
(Continued)

vectors, a candidate vector satisfying a vector condition in which an angle between the pupil center and a reference line is equal to or less than a predetermined threshold and determine that a pupil is located at a pupil center corresponding to the selected candidate vector.

10 Claims, 16 Drawing Sheets

(51) Int. Cl.
*A61B 3/02* (2006.01)
*A61B 3/00* (2006.01)
*A61B 3/113* (2006.01)
*A61B 3/11* (2006.01)
*G06K 9/00* (2006.01)

(58) Field of Classification Search
CPC ........... G06K 9/00604; G06K 9/00597; G06K 9/00281; G06K 9/00617; G06F 3/0346; A61B 3/103; A61B 3/14; A61B 3/113; A61B 3/1225; A61B 3/024; A61B 3/032; A61B 3/18; A61B 3/1015; A61B 3/158
USPC ....... 351/200, 210, 205, 206, 209, 221, 222, 351/240, 245, 246; 382/117
See application file for complete search history.

(56) References Cited

FOREIGN PATENT DOCUMENTS

| JP | 4452836 B2 | 4/2010 |
| WO | WO 2011/021936 A1 | 2/2011 |
| WO | WO 2013/176265 A1 | 11/2013 |
| WO | WO 2013176265 A1 * | 11/2013 .............. A61B 3/111 |

OTHER PUBLICATIONS

International Search Report dated Aug. 11, 2015 in corresponding PCT International Application No. PCT/JP2015/063586.
Written Opinion dated Aug. 11, 2015 in corresponding PCT International Application No. PCT/JP2015/063586.
H. Yamakawa et al., "Improved 3-Camera Pupil Detection of Targets Wearing Eyeglasses," The Journal of the Institute of Image Information and Television Engineers, vol. 68, No. 6, pp. J232-J237, May 23, 2014 (with English abstract).
K. Fukumoto et al., "Improvement of Robustness in Pupil Detection Assuming a Constant Interpupillary Distance in a Video-Based Eye-Gaze Detection System;—A Solution of Glasses Reflection Problem-," The Journal of the Institute of Image Information and Television Engineers, vol. 66, No. 12, pp. J504-J509, 2012 (with English abstract).
Extended European Search Report dated Dec. 22, 2017 issued in corresponding European Patent Application No. 15807498.9.

* cited by examiner

PUPIL DETECTION SYSTEM, GAZE DETECTION SYSTEM, PUPIL DETECTION METHOD, AND PUPIL DETECTION PROGRAM

CROSS-REFERENCE TO RELATED APPLICATIONS

The present application is a 35 U.S.C. §§ 371 national phase conversion of PCT/JP2015/063586, filed May 12, 2015, which claims priority to Japanese Patent Application No. 2014-118846, filed Jun. 9, 2014, the contents of both of which are incorporated herein by reference. The PCT International Application was published in the Japanese language.

TECHNICAL FIELD

The present invention relates to a pupil detection system, a gaze detection system, a pupil detection method, and a pupil detection program.

BACKGROUND ART

In the past, technique for detecting the pupil of a subject has been known. This technique is applicable to detection of an inattentive driving, detection of drowsiness of a driver, investigation of the degree of interest of a product, data input to a computer, and the like.

With respect to such pupil detection technique, the following Patent Literature 1 discloses a method of detecting a pupil based on a difference between a bright pupil image and a dark pupil image. The method detects the amount of difference in corneal reflection position between the two images imaging a bright pupil and a dark pupil and performs position correction in which one image is moved by an amount corresponding to the amount of difference in corneal reflection position to match the pupil portions of the both images substantially. Furthermore, the difference between the both images is obtained.

CITATION LIST

Patent Literature

[Patent Document 1] JP 4452836 B

SUMMARY OF INVENTION

Technical Problem

However, various noises may be easily caused in the bright pupil image and the dark pupil image. As an example of the noise, there is glasses reflection of light emitted from a light source. Among glasses reflections, there is a small glasses reflection enough not to be distinguished from corneal reflection. Also, since the position of glasses reflection moves largely depending on the movement of a person's head, it is difficult to distinguish the glasses reflection from the corneal reflection only based on characteristics of images. Also, in the case of a person having eyes moist with tears, a boundary between a lower eyelid and the white of the eye glows and the protrusion of the inner corner of the eye glows, which are similar to corneal reflection. When the noise is incorrectly detected as corneal reflection, position correction does not function correctly and, as a result, it is impossible to detect the pupil precisely. Therefore, it is preferable to correctly detect a pupil even when the pupil image includes a noise.

Solution to Problem

A pupil detection system according to one aspect of the present invention includes: a vector calculation unit configured to calculate a plurality of candidate vectors each connecting a corneal sphere center and a pupil center by a stereo method based on a first pupil image of a subject which is picked up by a first camera and a second pupil image of the subject which is picked up by a second camera, the corneal sphere center being an intersection point between an axis passing through the first camera and a corneal reflection point obtained from the first pupil image and an axis passing through the second camera and a corneal reflection point obtained from the second pupil image; and a determination unit configured to select, from among the plurality of candidate vectors, a candidate vector satisfying a vector condition in which an angle between the pupil center and a reference line, which is set based on a position of at least one of the first camera and the second camera, is equal to or less than a predetermined threshold and determine that a pupil is located at a pupil center corresponding to the selected candidate vector.

A pupil detection method according to one aspect of the present invention is a pupil detection method, which is performed by a pupil detection system including a processor, the pupil detection method including: a vector calculation step of calculating a plurality of candidate vectors each connecting a corneal sphere center and a pupil center by a stereo method based on a first pupil image of a subject which is picked up by a first camera and a second pupil image of the subject which is picked up by a second camera, the corneal sphere center being an intersection point between an axis passing through the first camera and a corneal reflection point obtained from the first pupil image and an axis passing through the second camera and a corneal reflection point obtained from the second pupil image; and a determination step of selecting, from among the plurality of candidate vectors, a candidate vector satisfying a vector condition in which an angle between the pupil center and a reference line, which is set based on a position of at least one of the first camera and the second camera, is equal to or less than a predetermined threshold and determining that a pupil is located at a pupil center corresponding to the selected candidate vector.

A pupil detection program according to one aspect of the present invention causes a computer to function as: a vector calculation unit configured to calculate a plurality of candidate vectors each connecting a corneal sphere center and a pupil center by a stereo method based on a first pupil image of a subject which is picked up by a first camera and a second pupil image of the subject which is picked up by a second camera, the corneal sphere center being an intersection point between an axis passing through the first camera and a corneal reflection point obtained from the first pupil image and an axis passing through the second camera and a corneal reflection point obtained from the second pupil image; and a determination unit configured to select, from among the plurality of candidate vectors, a candidate vector satisfying a vector condition in which an angle between the pupil center and a reference line, which is set based on a position of at least one of the first camera and the second camera, is equal to or less than a predetermined threshold and determine that a pupil is located at a pupil center corresponding to the selected candidate vector.

According to these aspects, the plurality of candidate vectors each connecting the corneal sphere center and the pupil center are calculated, among them, a candidate vector of which the direction is regarded as being correct is selected, and it is determined that a pupil is located at the pupil center corresponding to the selected vector. As described above, it is possible to correctly detect a pupil by checking a direction with respect to each of a plurality of candidate vectors even when the pupil image includes a noise.

Advantageous Effects of Invention

According to one aspect of the present invention, it is possible to correctly detect a pupil even when the pupil image includes a noise.

DESCRIPTION OF EMBODIMENTS

Figure 1:
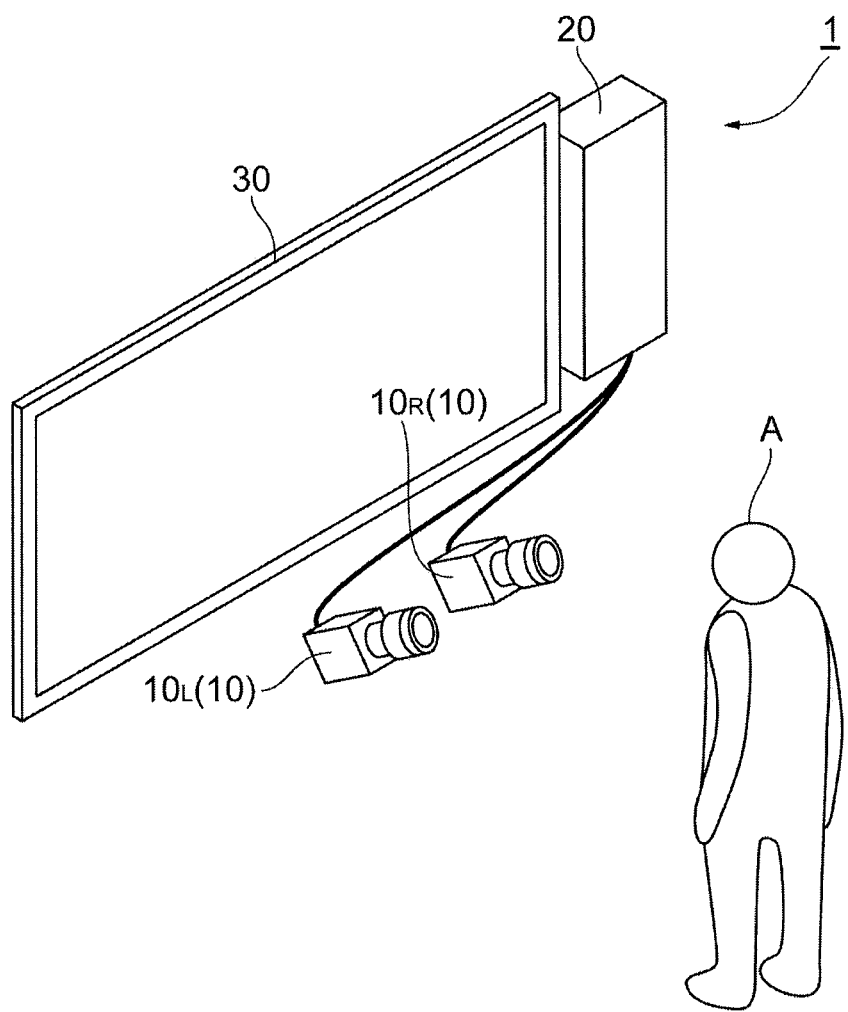
FIG. 1 is a perspective view illustrating a pupil detection system according to an embodiment.

Hereinafter, embodiments of the present invention will be described below in detail with reference to the accompanying embodiment. Note that, in the description of the drawings, the same elements are denoted by the same reference numerals and a redundant description thereof is omitted.

[Configuration of Pupil Detection System]

First, a configuration of a pupil detection system 1 according to an embodiment will be described with reference to FIGS. 1 to 4. The pupil detection system 1 is a computer system that detects a position of a pupil of a subject and a pupil detection method according to the present embodiment is performed by the system. The subject is a person of which the pupil position is to be detected, and can be referred to as a subject person. The purpose to use the pupil detection system 1 and the pupil detection method is not limited, and the pupil detection system 1 can be used for, for example, detection of inattentive driving, detection of driver's drowsiness, investigation of degree of interest on products, data input to computer, etc.

As schematically illustrated in FIG. 1, the pupil detection system 1 includes a pair of cameras (first camera and second camera) 10 functioning as a stereo camera and an image processing device 20. Herein, if necessary, the pair of cameras 10 includes a left camera $10_L$ located on the left of the subject A and a right camera $10_R$ located on the right of the subject A. In the present embodiment, the pupil detection system 1 further includes a display device 30 which is a subject viewed by the subject A. The use purpose of the pupil detection system 1 is not, however, limited to as those described above. Objects in the gaze direction of the subject A are not limited to the display device 30 and may be, for example, the front glass of a vehicle. Therefore, the display device 30 is not an essential element in the pupil detection system 1. Each of the cameras 10 is connected to the image processing device 20 in a wireless or wired manner and various types of data or commands are transmitted between the camera 10 and the image processing device 20. Camera correction is performed in advance with respect to each of the cameras 10.

The camera 10 is used to photograph the pupil of the subject A and the surroundings thereof. The pair of cameras 10 are arranged at a predetermined interval in a horizontal direction, and are disposed to be lower than the face of the subject A in order to prevent reflected light from being picked up in a face image when the subject A is wearing glasses. An elevation angle of the camera 10 in the horizontal direction is set to be in a range from 20 degrees to 35 degrees in consideration of pupil detection and avoidance of interference of the visual field of the subject A. Camera correction is performed in advance with respect to each of the cameras 10.

In the present embodiment, the camera 10 is an NTSC type camera that is one of interlace scan systems. In the NTSC scheme, image data of one frame, which is obtained at 30 frames per second, consists of an odd field consisting of odd-numbered horizontal pixel lines and an even field consisting of even-numbered horizontal pixel lines, and is generated by alternately picking up an image of the odd field and an image of the even field at 1/60 second. Therefore, one frame corresponds to a pair of odd field and even field. The camera 10 images a subject A in response to a command from the image processing device 20 and outputs image data to the image processing device 20.

Figure 2:
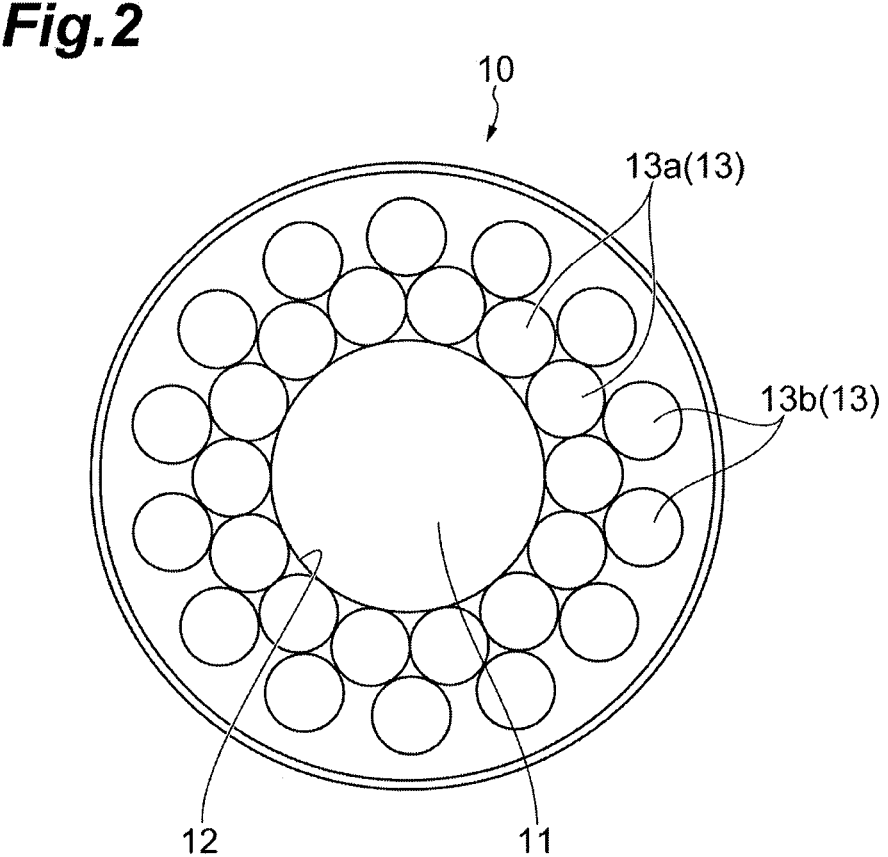
FIG. 2 is a plan view illustrating a lens portion of a camera.

The lens portion of the camera 10 is schematically illustrated in FIG. 2. As illustrated in FIG. 2, in the camera 10, an objective lens 11 is arranged in an aperture 12 having a circular shape, and a light source 13 is provided on the outside of the aperture 12. The light source 13 is a device which irradiates a face of the subject A with illumination light and includes a plurality of light-emitting elements 13a and a plurality of light-emitting elements 13b. The light-emitting elements 13a are semiconductor light-emitting elements (LED) in which output light has a central wavelength of 850 nm and are arranged in a ring shape at equal intervals along the edges of the aperture 12. The light-emitting elements 13b are semiconductor light-emitting elements in which output light has a central wavelength of 940 nm and are arranged in a ring shape at equal intervals on the outside of the light-emitting elements 13a. Therefore, a distance from an optical axis of the camera 10 to the light-emitting elements 13b is larger than a distance from the optical axis to the light-emitting elements 13a. Each of the light-emitting elements 13a and 13b are provided to emit illumination light along the optical axis of the camera 10. The arrangement of the light source 13 is not limited to the configuration illustrated in FIG. 2 and another arrangement is possible as long as the camera is regarded as a pinhole model.

The image processing device 20 is a computer that performs control of the camera 10 and detection of a pupil of the subject A. The image processing device 20 may be implemented by a stationary or portable personal computer (PC), a workstation, or another type of computer. Also, the image processing device 20 may be implemented by combining a plurality of computers of arbitrary types. In the case of using a plurality of computers, the computers are connected via a communication network, such as the Internet or an intranet.

Figure 3:
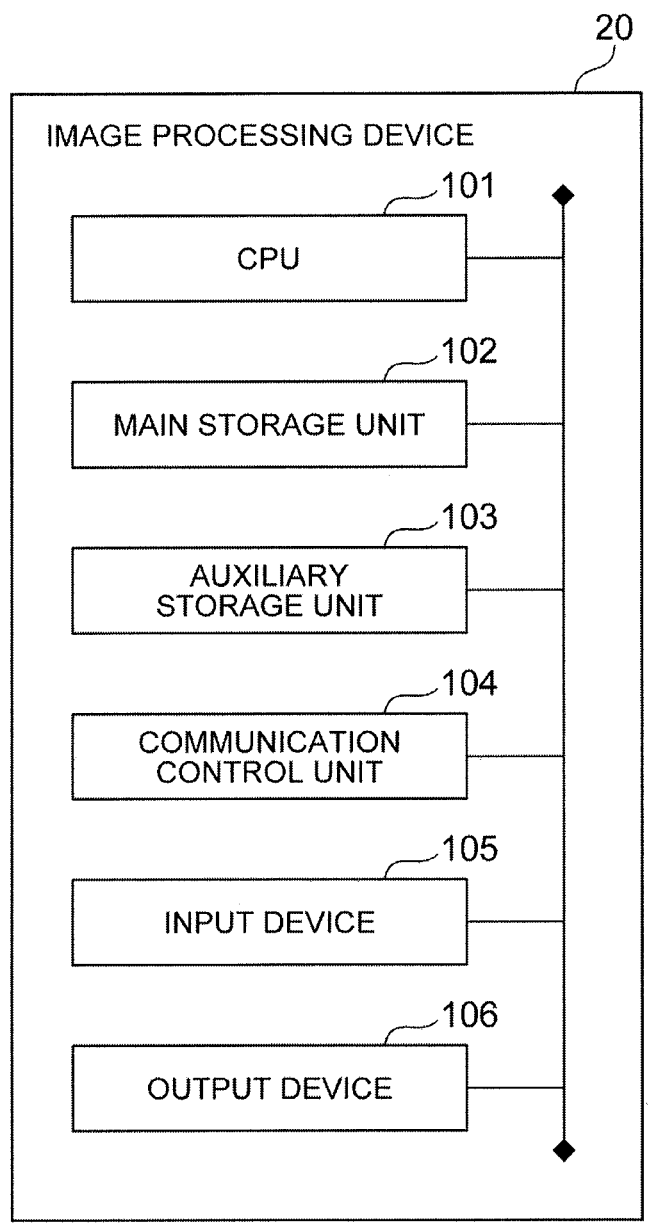
FIG. 3 is a diagram illustrating a hardware configuration of an image processing device according to an embodiment.

A general hardware configuration of the image processing device 20 is illustrated in FIG. 3. The image processing device 20 includes a CPU (processor) 101 which performs an operating system or an application program or the like, a non-transitory main storage unit 102 which is configured by ROM and RAM, a non-transitory auxiliary storage unit 103 which is configured by a hard disk, a flash memory or the like, a communication control unit 104 which is configured by a network card or a wireless communication module, an input device 105 such as a keyboard, a mouse, or the like, and an output device 106 such as a display, a printer, or the like.

Each functional element of the image processing device 20 to be described below is implemented by loading predetermined software on the CPU 101 or the main storage unit 102, operating the communication control unit 104, the input device 105, the output device 106, or the like, under the control of the CPU 101, and reading and writing data in the main storage unit 102 or the auxiliary storage unit 103. Data or database necessary for processing is stored in the main storage unit 102 and the auxiliary storage unit 103.

Figure 4:
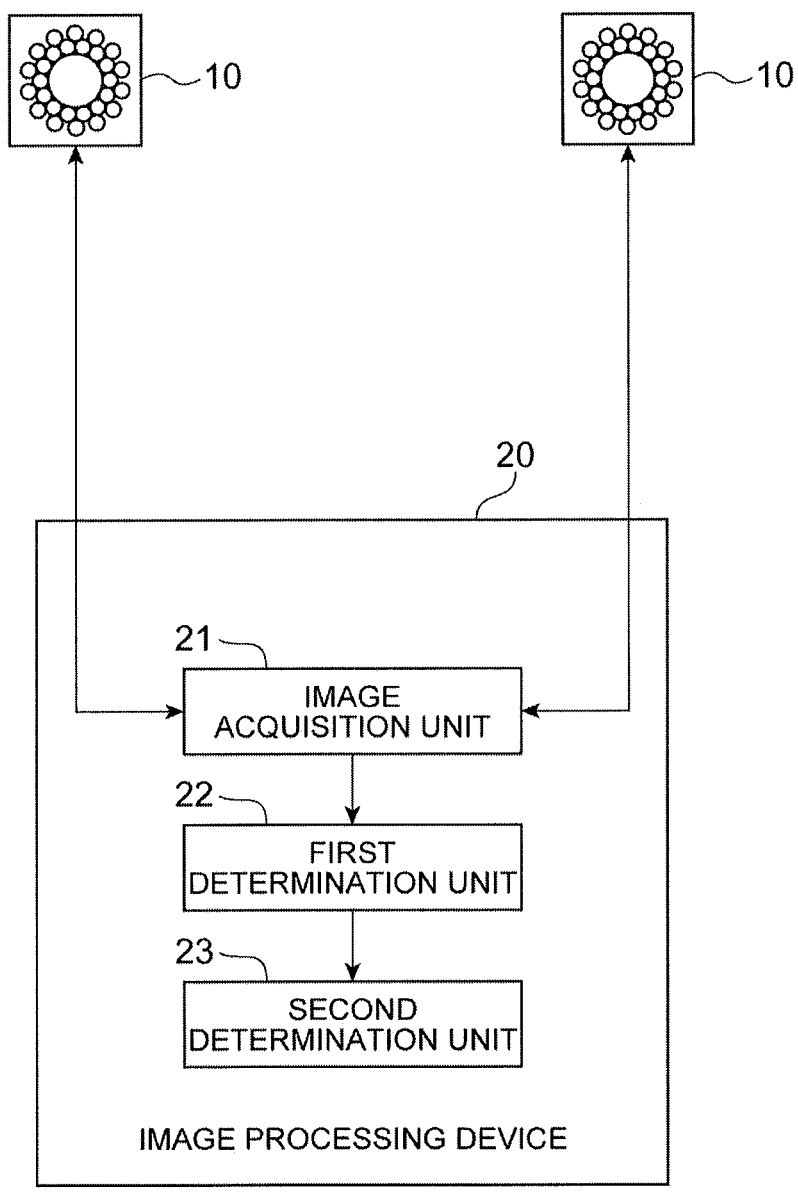
FIG. 4 is a block diagram of a functional configuration of a pupil detection system according to an embodiment.

As illustrated in FIG. 4, the image processing device 20 includes an image acquisition unit 21, a first determination unit (vector calculation unit and determination unit) 22, and a second determination unit (determination unit) 23. The image acquisition unit 21 is a functional element that acquires image data from the camera 10 by controlling an image pickup timing of the camera 10 and a light emission timing of the light source 13 of the camera 10. The first determination unit 22 is a functional element that determines a position of a pupil based on a candidate vector which can be obtained from the image data. The second determination unit 23 is a functional element that calculates a gaze based on the position of the pupil which is determined as being correct in the first determination unit 22 and further determines the position of the pupil based on the gaze. The gaze is a line connecting a center of the pupil of the subject and a gaze point of the subject (point viewed by the subject). Also, the term "gaze" may include the meaning (concept) of a start point, an end point and a direction. The image processing device 20 determines (estimates) a correct pupil position through two-step determination. The output of a result of determination of the pupil position is not limited at all. For example, the image processing device 20 may display the result of the determination on a monitor in image, figure, or text form, store the result in a storage unit such as memory or database, or transmit the result to another computer system via a communication network.

In this specification, "candidate vector" refers to a vector connecting a corneal sphere center and a pupil center (for example, a vector from a corneal sphere center to a pupil center), and therefore, may be referred to as "corneal sphere center-pupil center vector". However, since the corneal sphere center and the pupil center, which are an edge node of the candidate vector, are obtained by calculation, and thus can be different from the actual corneal sphere center and pupil center of the subject A.

[Pupil Detection Method]

Next, the operation of the pupil detection system 1 will be described and a pupil detection method according to the present embodiment will be described, with reference to FIGS. 5 to 15.

(Overview of Processing)

Figure 5:
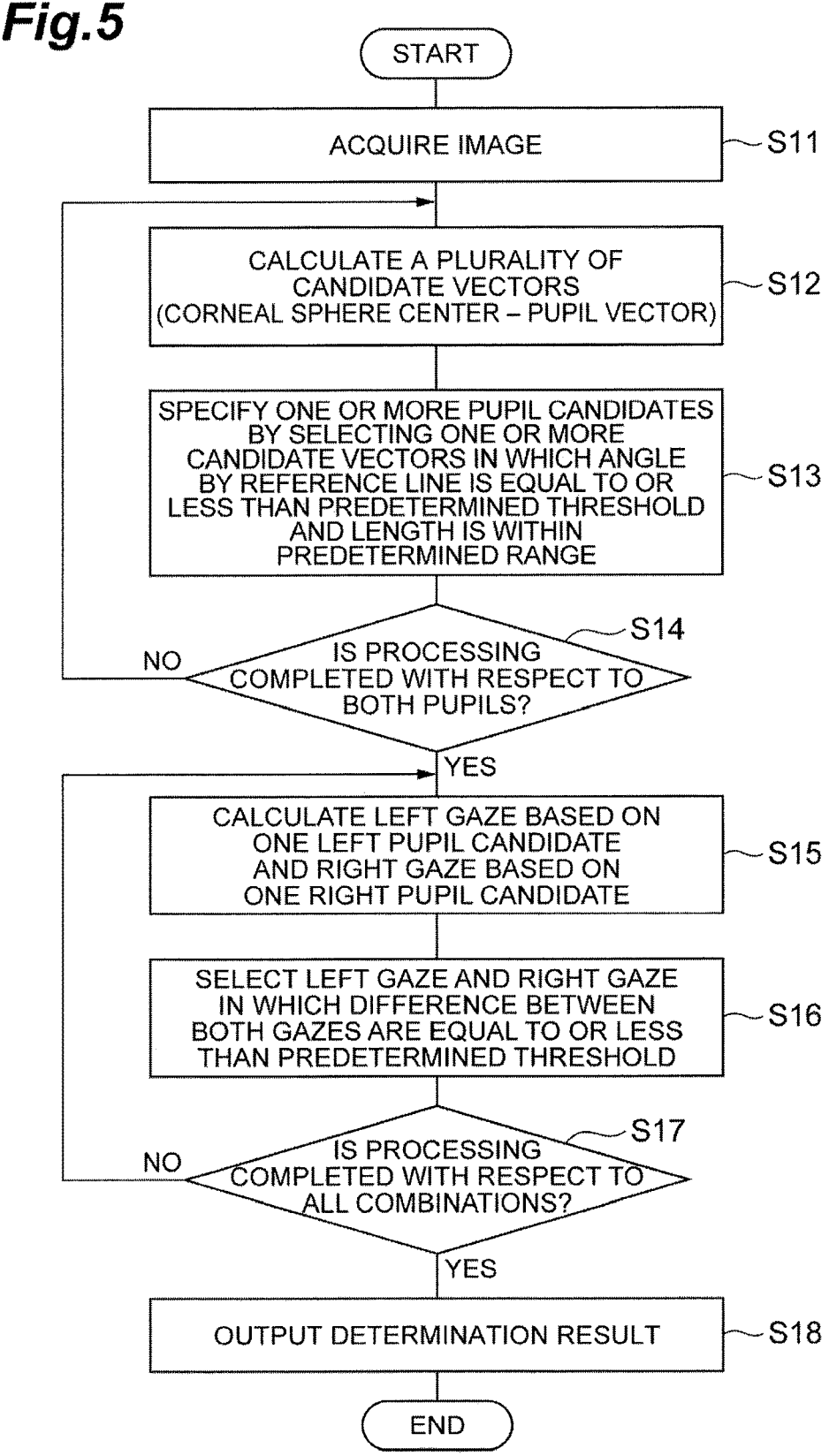
FIG. 5 is a flowchart of an operation of a pupil detection system according to an embodiment.

The overview of the pupil detection method is illustrated in FIG. 5. First, the image acquisition unit 21 acquires a bright pupil image and a dark pupil image from each of the cameras 10 (step S11). Subsequently, the first determination unit 22 calculates a plurality of candidate vectors based on the bright pupil image and the dark pupil image (step S12, vector calculation step). The first determination unit 22 selects a candidate vector satisfying a condition consisting the two items below (in the present embodiment, "vector condition") from among a plurality of candidate vectors to specify one or more pupil candidates (pupil positions determined as being correct) (step S13, determination step).

Vector condition (1): an angle between the candidate vector and a reference line is equal to or less than a predetermined threshold.

Vector condition (2): a length of the candidate vector is within a predetermined range.

The first determination unit 22 specifies the pupil position satisfying the vector condition with respect to both pupils (see step S14).

Subsequently, the second determination unit 23 further performs determination based on one or more left pupil candidates (left pupil candidate group) and one or more right pupil candidates (right pupil candidate group). Specifically, the second determination unit 23 calculates a left gaze based on one left pupil candidate selected from the left pupil candidate group and calculates a right gaze based on one right pupil candidate selected from the right pupil candidate group (step S15). In addition, the second determination unit 23 selects a left gaze and a right gaze satisfying the below-described condition (in this specification, referred to as "gaze condition") (step S16).

Gaze condition: a difference between a left gaze and a right gaze in a height direction of the subject is equal to or less than a predetermined threshold.

The second determination unit 23 performs the processing of steps S15 and S16 with respect to all combinations of the left pupil candidate and the right pupil position (see step S17) and outputs a final determination result (step S18).

Figure 6:
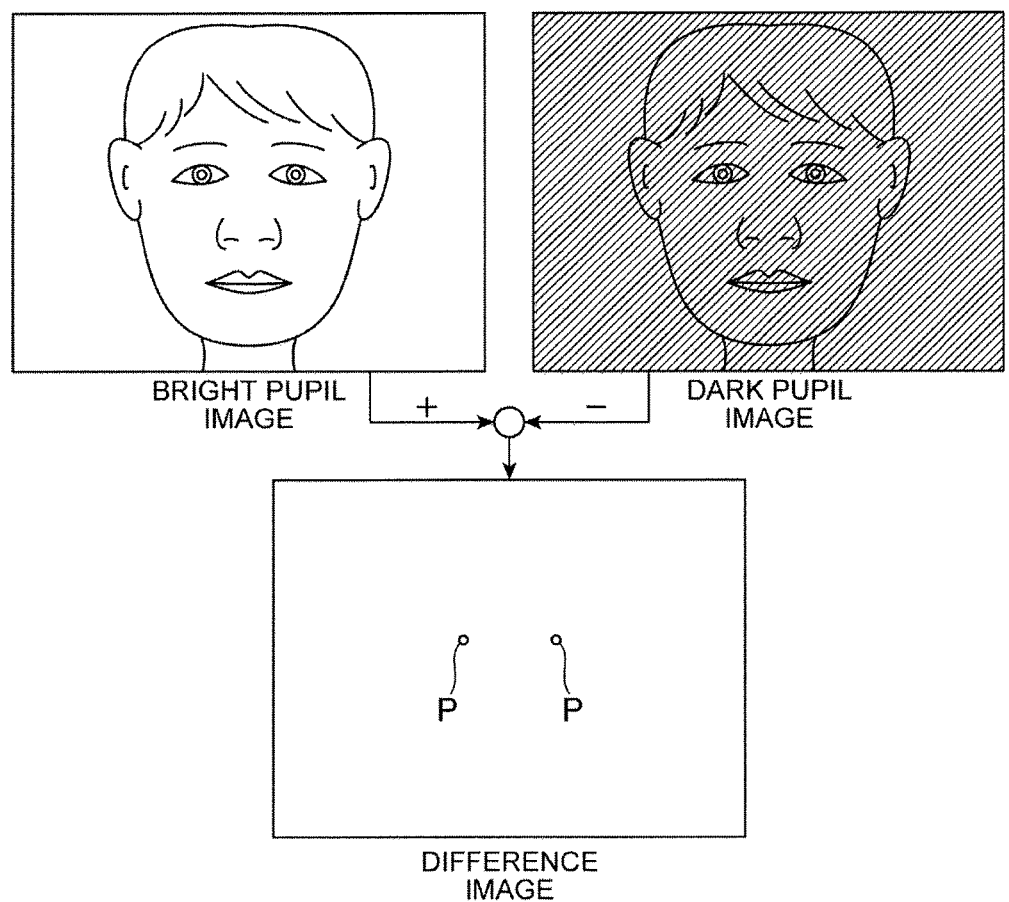
FIG. 6 is a diagram illustrating generation of a difference image.
Figure 7:
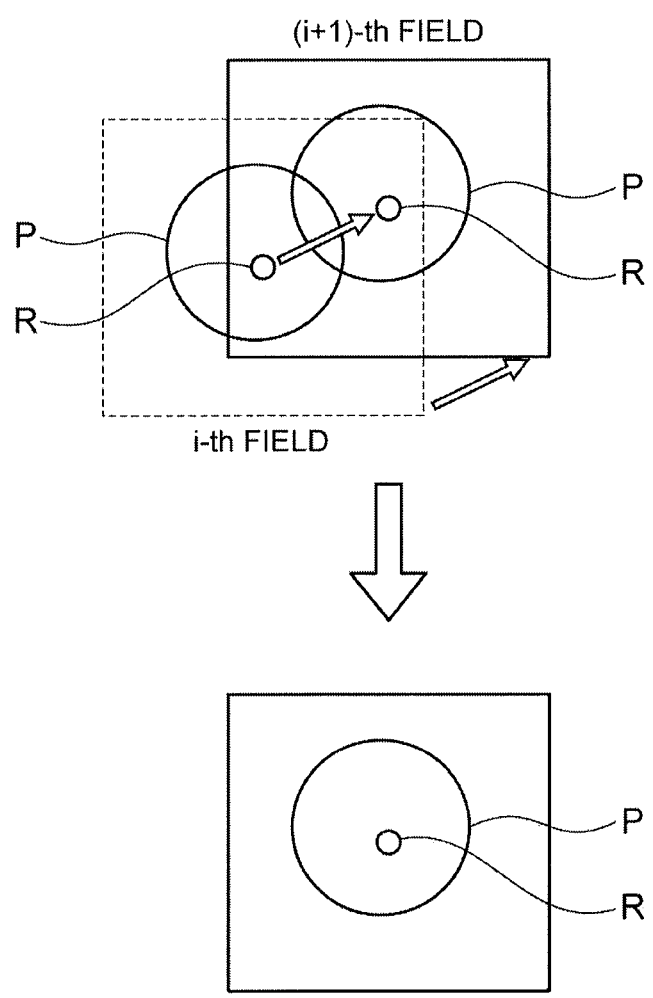
FIG. 7 is a diagram for describing position correction based on corneal reflection.

When the head of the subject A does not move before an (i+1)-th field image is picked up after an i-th field image has been picked up, as illustrated in FIG. 6, a difference image in which a pupil portion (symbol P in FIG. 6) emerges can be generated by merely taking a difference between the bright pupil image and the dark pupil image. However, when the head of the subject A moves within a period of time before the (i+1)-th field image is picked up after the i-th field image has been picked up, a difference in position of the pupil between the two images occurs, and as a result, a good difference image cannot be obtained. Therefore, before the difference image is obtained, position correction is performed on the bright pupil image and the dark pupil image based on the corneal reflection.

In position correction based on the corneal reflection, the i-th field (image) is shifted such that the positions of corneal reflection points R respectively detected from the i-th field (image) and the (i+1)-th field (image) match each other (refer to arrows in FIG. 7), and therefore, a difference between the two images is obtained. It is possible to detect a pupil P from the difference image illustrated in the lower end of FIG. 7.

Figure 8:
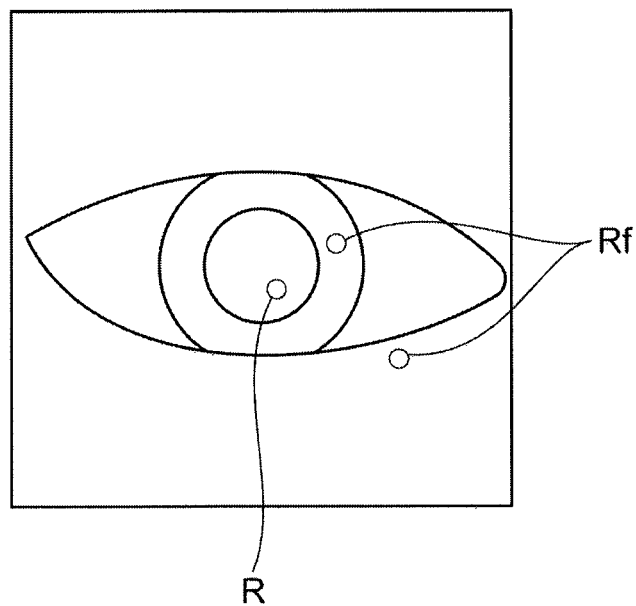
FIG. 8 is a diagram illustrating a noise of corneal reflection.

However, in the bright pupil image and the dark pupil image, various noises such as glasses reflection of light may be easily placed. For example, as illustrated in FIG. 8, noises Rf, which are small enough not to be distinguished from a genuine corneal reflection point R, can be picked up in the pupil image. When position correction is performed on one of the noises Rf as a correct corneal reflection point, a correct pupil position cannot be obtained. The purpose of the pupil detection system 1 is to specify a correct pupil position even when a noise is picked up in the pupil image.

(Acquisition of Pupil Image)

Light entering an eye is irregularly reflected by a retina and light passing though a pupil from among the reflected light has a property of returning to a light source with strong directivity. When the camera is exposed to the light in a case in which the light source disposed in the vicinity of the aperture of the camera emits light, a part of light reflected from the retina enters the aperture, thus obtaining an image in which the pupil is imaged more brightly than the vicinity of the pupil. This image is the bright pupil image. In this regard, when the camera is exposed to the light in a case in which the light source apart from the aperture of the camera emits light, light entering an eye does not almost return to the aperture of the camera, thus obtaining an image in which the pupil is darkly imaged. This image is the dark pupil image. Also, when an eye is irradiated with light having a wavelength of high transmittance, the pupil is brightly picked up because the large amount of light is reflected by a retina, and when an eye is irradiated with light having a wavelength of low transmittance, the pupil is darkly picked up because the small amount of light is reflected by a retina.

In the present embodiment, the light-emitting element 13a emitting light having a wavelength of high transmittance (central wavelength is 850 nm) is disposed at a position adjacent to the aperture 12, and the light-emitting element 13b emitting light having a wavelength of low transmittance of the eye (central wavelength is 940 nm) is spaced apart from the aperture 12. The image acquisition unit 21 picks up a bright pupil image by lighting the light-emitting element 13a in compliance with odd numbered fields of the camera 10 and picks up a dark pupil image by lighting the light-emitting element 13a in compliance with even numbered fields of the camera 10. The image acquisition unit 21 slightly shifts an operation timing between the two cameras 10 and an exposure time of each of the cameras 10 is set to be equal to or shorter than the shifted time. The image acquisition unit 21 alternately lights the light-emitting element 13a and the light-emitting element 13b during the exposure time of each of the cameras 10, thus allowing the light from the light source 13 of one of the cameras 10 not to influence an image of the other of the cameras 10 (so that crosstalk does not occur).

The image acquisition unit 21 acquires the bright pupil image and the dark pupil image obtained by such a series of control. The bright pupil image or the dark pupil image obtained by one of the cameras 10 corresponds to a first pupil image, and the bright pupil image or the dark pupil image obtained by the other of the cameras 10 corresponds to a second pupil image. Since the obtained image data has valid pixels only in the odd numbered fields or the even numbered field, the image acquisition unit 21 generates the bright pupil image and the dark pupil image by embedding a brightness mean of pixel lines of the valid pixels adjacent to each other into a pixel value between the lines. The image acquisition unit 21 outputs the bright pupil image and the dark pupil image to the first determination unit 22.

(Position Correction Based on Corneal Reflection)

The first determination unit 22 detects one or more candidates of a corneal reflection point (corneal reflection candidate point) from each of the bright pupil image and the dark pupil image, which are input from the image acquisition unit 21. Specifically, the first determination unit 22 performs binarization and labeling by a P-tile method on a sheet of image, and selects one or more corneal reflection candidate points from the image based on information such as a shape or the brightness mean. By the above processing, the first determination unit 22 may obtain the one or more (for example, several) corneal reflection candidate points from each of the bright pupil image and the dark pupil image. The maximum number of corneal reflection candidate points (for example, 2, 3, 5, or the like) obtained from a single pupil image may be previously set. For example, the first determination unit 22 detects three corneal reflection candidate points indicated by reference symbols R and Rf, from the image illustrated in FIG. 8.

Subsequently, the first determination unit 22 selects one corneal reflection candidate point from each of the bright pupil image and the dark pupil image, and calculates a movement amount of corneal reflection between the two images as a position correction amount, based on the two selected corneal reflection candidate points. Next, the first determination unit 22 generates a difference image from the two images obtained by shifting an image of a previous field (i-th field) to an image of a next field ((i+1)-th field) by the position correction amount such that the two corneal reflection candidate points match each other. The first determination unit 22 acquires a position of the corneal reflection candidate points which match each other.

(Calculation of Pupil Position and Corneal Reflection Position)

Subsequently, the first determination unit 22 specifies candidates of the pupil position from the difference image. Specifically, the first determination unit 22 use performs binarization of the difference image by setting a half value of the mean brightness thereof as a threshold value in such a way that the brightness mean of the pupil detected from the previous frame is used by using the fact that there is no large change in brightness from the previous frame. Then, the first determination unit 22 selects pupil candidates from among connection components of a pixel assigned a label and calculates central coordinate(s) of each pupil candidate, based on shape parameters, such as a pupil-like area, size, area ratio, square degree, or pupil feature amount. Therefore, it is possible to obtain the coordinates of one or more pupil candidates with respect to the coordinates of the corneal reflection candidate points which match each other.

On the other hand, there may be a case in which no coordinates of pupil candidate are obtained with respect to the coordinates of the corneal reflection candidate points which match each other. This may be caused when one or both corneal reflection candidate points are fake corneal reflection candidate points. In this case, the first determination unit 22 may exclude the corneal reflection candidate points which match each other. By excluding the corneal reflection candidate points estimated as the fake corneal reflection candidate points before a stereo method (stereo matching) to be described below is performed, it is possible to reduce a time for subsequent calculation.

Subsequently, the first determination unit 22 calculates three-dimensional coordinates of each pupil candidate. Specifically, the first determination unit 22 calculates three-dimensional positions of left and right pupils from the calculated central coordinates of the pupils by using the stereo method. The stereo method is a method of previously measuring internal parameters such as a focus distance of lens of a camera, a center of an image, and a size of an image and external parameters such as a position and attitude of the camera and, when a subject is photographed by several stereo cameras, determining a spatial position of a point of the image by using the internal parameters and the external parameters based on the coordinates of that point.

Figure 9:
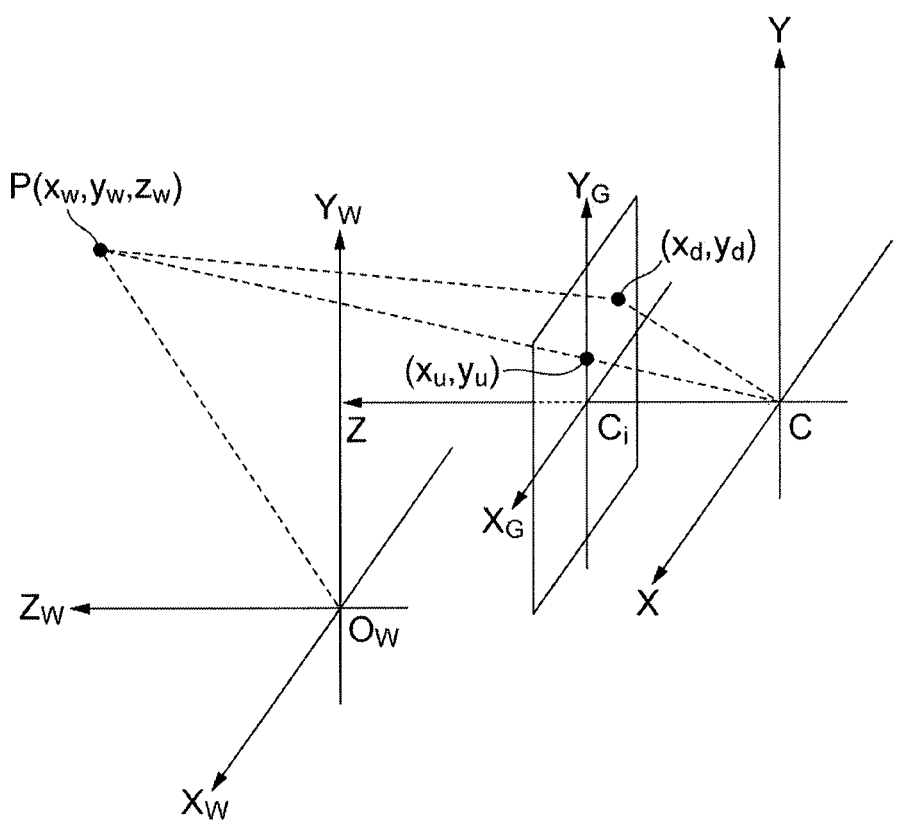
FIG. 9 is a diagram illustrating position relationship of a coordinate system set in a pupil detection system according to an embodiment.

The first determination unit 22 uses a coordinate system as illustrated in FIG. 9 when calculating three dimensional coordinates of the pupil using the stereo method. The world coordinate system ($X_W$, $Y_W$, $Z_W$) illustrated in the same drawing is a coordinate system in which an origin point $O_W$ shared by the two cameras 10 is placed at, for example, a screen center of the display device 30. The camera coordinate system (X, Y, Z) is a coordinate system in which the origin point C is an optical center of the camera 10 and a Z axis is parallel to an optical axis perpendicularly drawn from the optical center to an image surface. An image coordinate system ($X_G$, $Y_G$) is a coordinate system which is parallel to an XY plane along the image surface on which imaging element is placed and has, as an origin point $C_i$, an intersection point (image center) between the optical axis and the image plane. When the point P is coordinates of a target point, a projected point ($X_d$, $Y_d$) onto the image coordinate system in the case of using the camera 10 is misaligned from an ideal projected point ($X_u$, $Y_u$) due to image distortion. Therefore, in order to precisely measure a three-dimensional position using the stereo method, it is required to previously obtain calibration data recording association between the world coordinates of a target point P and the image coordinates thereof. For example, as external parameters, a parallel movement vector of a camera coordinate system with respect to the world coordinate system and a rotation matrix of the camera coordinate system with respect to the world coordinate system, or, as an internal parameters, a focus distance, image center coordinates, a scale coefficient, a lens distortion coefficient, a gap between imaging elements and the like are previously obtained as the calibration data and are stored in the first determination unit 22.

The first determination unit 22 obtains relational expressions of pupil center coordinates of the image coordinate system detected based on output data from the two cameras 10 and pupil center coordinates of the world coordinate system, referring to calibration data. Next, the first determination unit 22 obtains three-dimensional coordinates of a pupil of a subject A on the world coordinate system, from two relational expressions. Similarly, the first determination unit 22 can obtain three-dimensional coordinates of left and right pupils of the subject A.

Also, the first determination unit 22 calculates central coordinates between a corneal reflection point corresponding to the left camera $10_L$ (obtained from an image of the left camera $10_L$) and a corneal reflection point corresponding to the right camera $10_R$ (obtained from an image of the right camera $10_R$) by using the same method as the calculation of the three-dimensional coordinates of the pupil candidate.

In the case of performing the processing of previously excluding a corneal reflection candidate point regarded as fake corneal reflection, the first determination unit 22 may calculate the central coordinates of the remaining corneal reflection points (corneal reflection candidate points) which are not excluded.

(Calculation of Candidate Vector)

Subsequently, the first determination unit 22 calculates a candidate vector. The calculation will be described with reference to FIGS. 10 and 11. The first determination unit 22 sets, as three-dimensional coordinates of a corneal sphere center, three-dimensional coordinates of an intersection point C of a straight line (axis) $L_L$ passing through a lens center of the left camera $10_L$ (other points than the lens center may be possible) and a corneal reflection point (corneal reflection candidate point) $R_L$ corresponding to the left camera $10_L$ and a straight line (axis) $L_R$ passing through a lens center of the right camera $10_R$ (other points than the lens center may be possible) and a corneal reflection point (corneal reflection candidate point) $R_R$ corresponding to the right camera $10_R$. The first determination unit 22 calculates a candidate vector V based on the three-dimensional coordinates of the corneal sphere center C and the pupil center P.

Since the first determination unit 22 can detect one or more pupil candidates from a set of corneal reflection candidate points selected from the bright pupil image and the dark pupil image, the first determination unit 22 obtains one or more candidate vectors from the set of corneal reflection candidate points. On the other hand, the first determination unit 22 does not generate candidate vectors corresponding to excluded corneal reflection candidate points. That is, the first determination unit 22 calculates only candidate vectors corresponding to the corneal reflection candidate points that were not excluded, thus reducing calculation time accordingly. The first determination unit 22 obtains a plurality of candidate vectors by performing the above-described processing on all of combinations of corneal reflection candidate points of the bright pupil image and corneal reflection candidate points of the dark pupil image. For example, it is assumed that, with respect to the left camera $10_L$, two corneal reflection candidate points are detected from the bright pupil image and three corneal reflection candidate points are detected from the dark pupil image. In this case, when a genuine corneal reflection point is included in both the bright pupil image and the dark pupil image, the first determination unit 22 can calculate at most six and at least one candidate vectors based on six (=2×3) difference images with respect to the left camera $10_L$. Also, it is assumed that, with respect to the right camera $10_R$, two corneal reflection candidate points are detected from each of the bright pupil image and the dark pupil image. In this case, when a genuine corneal reflection point is included in both the bright pupil image and the dark pupil image, the first determination unit 22 can calculate at most four and at least one candidate vectors based on four (=2×2) difference images with respect to the right camera $10_R$. In this case, eventually, at most 24 (=6×4) and at least one (=1×1) candidate vectors can be obtained due to stereo matching.

(Determination of Candidate Vector)

Figure 10:
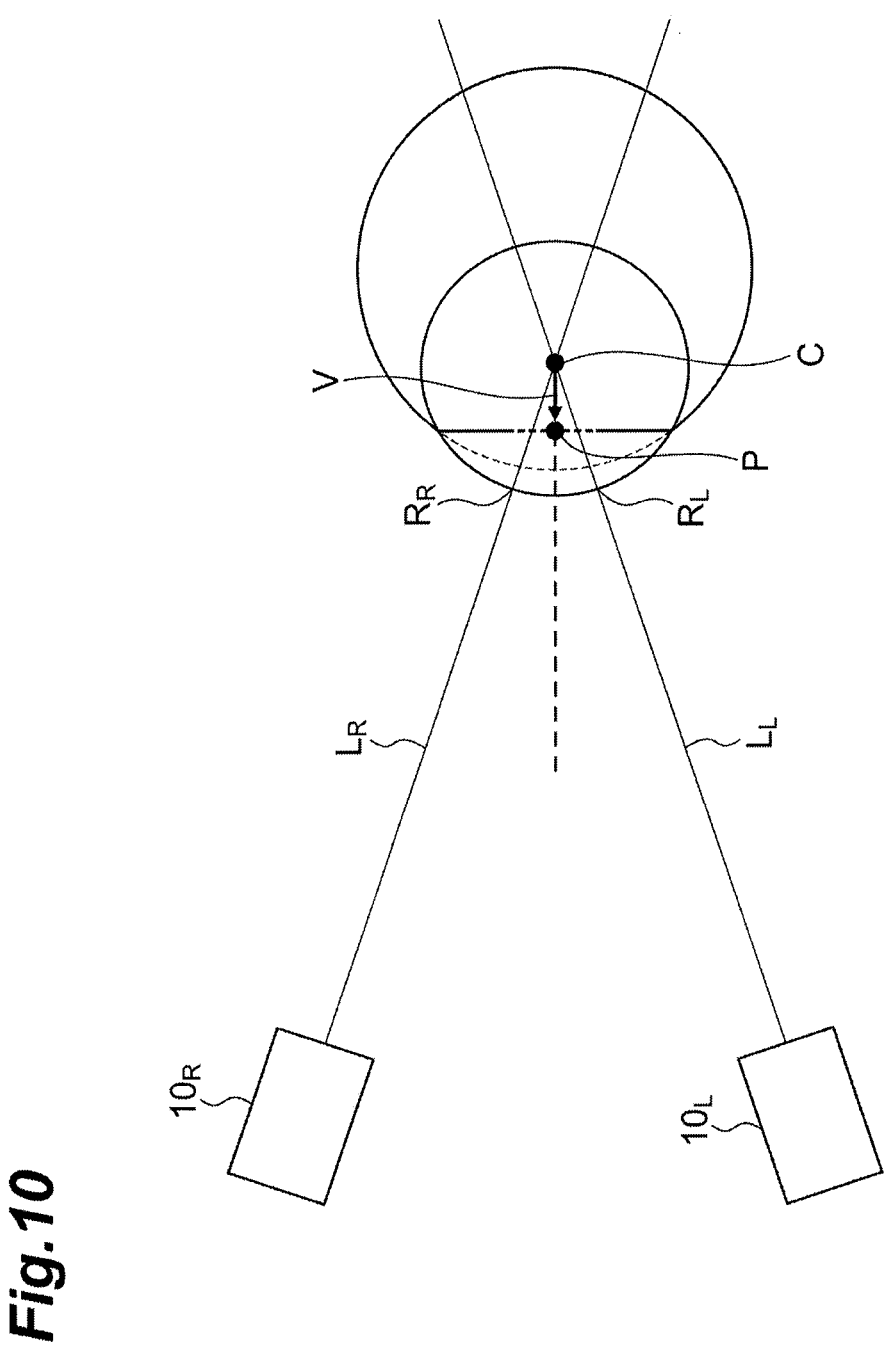
FIG. 10 is a diagram illustrating an example of a candidate vector (corneal sphere center–pupil vector).
Figure 11:
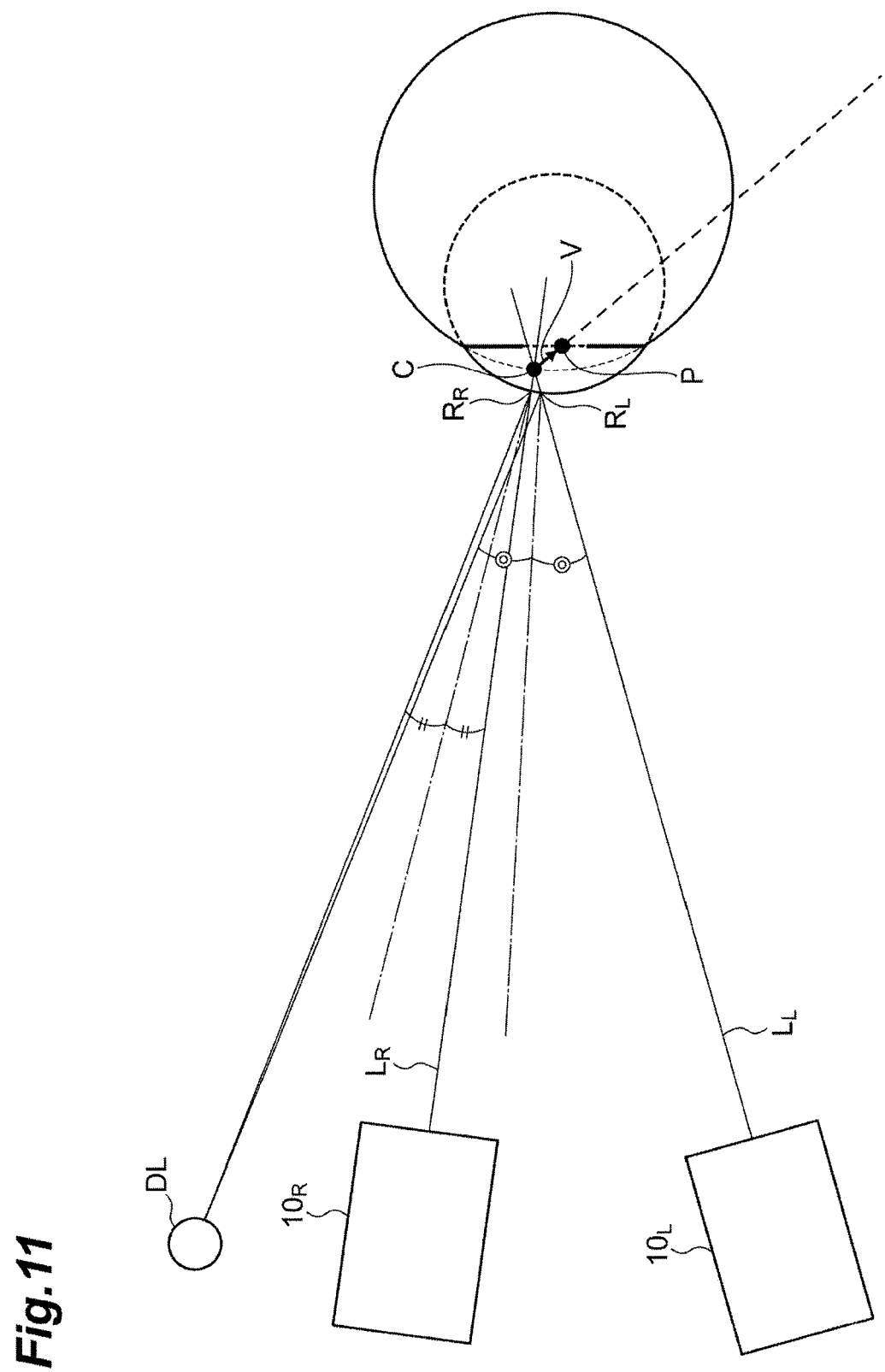
FIG. 11 is a diagram illustrating another example of a candidate vector (corneal sphere center–pupil vector).

The obtained candidate vectors may include a candidate vector V considered as being correct as illustrated in FIG. 10 or a candidate vector V calculated based on corneal reflection by a disturbance light source DL (not regarded as being correct), as illustrated in FIG. 11. The first determination unit 22 determines whether each candidate vector satisfies a vector condition and selects only candidate vectors satisfying the vector condition. As described above, the vector condition is a condition in which an angle between the candidate vector and a reference line is equal to or less than a predetermined threshold and a length of the candidate vector is within a predetermined range.

Figure 12:
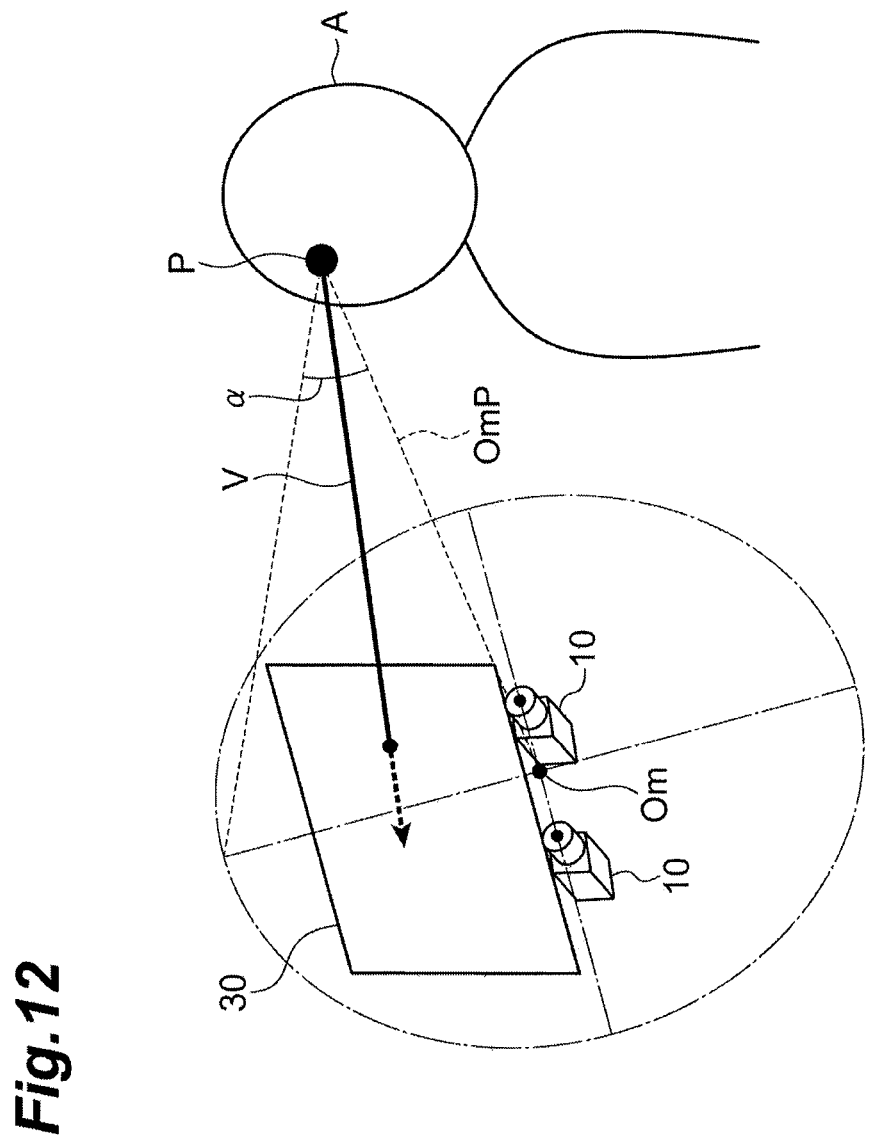
FIG. 12 is a diagram for describing vector conditions.

In the example of FIG. 12, a reference line used in the vector condition is a line OmP connecting a central point (center of mass) Om between the lens centers of the two cameras 10 and the pupil center P. The threshold α used in the vector condition may be 30 degrees, 40 degrees, or 50 degrees, or may be another value. The first determination unit 22 selects the candidate vector V when an angle between the candidate vector V and the reference line OmP is equal to or less than the threshold α and excludes the candidate vector V when the angle exceeds the threshold α. Also, in FIG. 12, the candidate vector V is illustrated longitudinally in the direction of the camera 10 in order for description.

The reference line may be a line connecting the lens center of one of the cameras 10 and the pupil center P. In any case, the reference line is set based on the pupil center and a position of at least one camera 10.

The first determination unit 22 may determine whether a length of the candidate vector V, that is, a distance between the pupil center and the corneal sphere center is within the predetermined range. For example, the lower limit and upper limit of the range are respectively d 1.5 (mm) and d+1.5 (mm). In this case, the value d is a distance between a corneal sphere center and a pupil center, measured with respect to one or more users, in an environment in which glasses reflection or fake corneal reflection does not occur. Also, the lower limit of the range may be d−1.0 (mm) and d−2.0 (mm), and the upper limit of the range may be d+1.0 (mm) and d+2.0 (mm). The first determination unit 22 selects the candidate vector V when the length of the candidate vector V is within the range and excludes the candidate vector V when the length is out of the range.

The first determination unit 22 specifies the three-dimensional coordinates of the pupil center corresponding to the candidate vector V satisfying the vector condition, as a pupil candidate. The first determination unit 22 specifies pupil candidates of left and right pupils (hereinafter, referred to as left pupil candidate and right pupil candidate) and outputs data of the pupil candidates to the second determination unit 23. Specifying a pupil center corresponding to the candidate vector satisfying the vector condition means determining that a pupil is located at the pupil center.

(Detection of Gaze)

Figure 13:
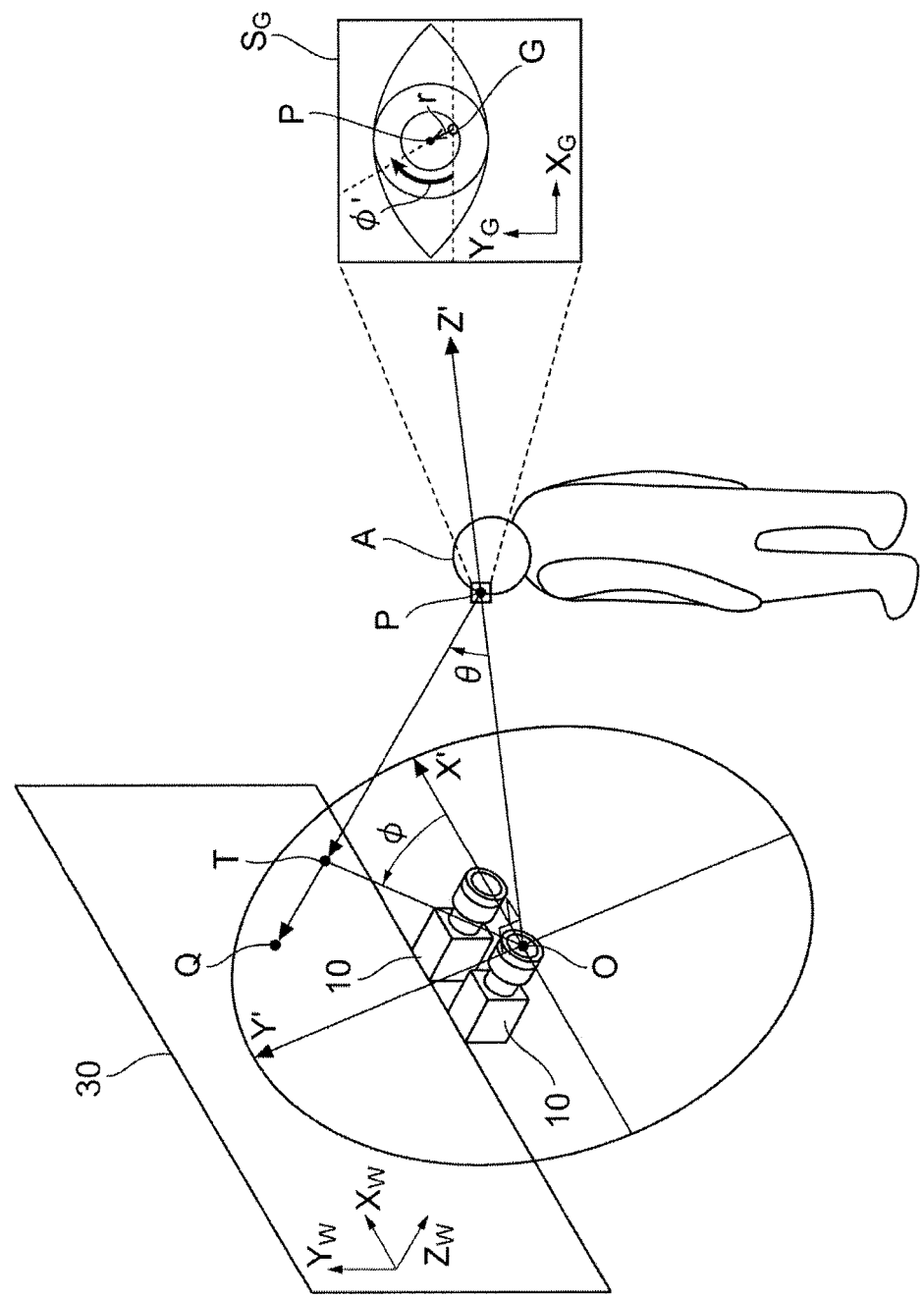
FIG. 13 is a diagram for describing gaze detection.

The second determination unit 23 detects a gaze based on the three-dimensional coordinates of the left and right pupils. As illustrated in FIG. 13, based on the three-dimensional position P of the pupil, a virtual gaze plane X'-Y' is considered in which a center of the aperture 12 of the camera 10 is set as an origin point O, and the reference line OP connecting the origin point O and the pupil center P is set as a normal line. Herein, X' axis corresponds to an intersection line between the $X_W$-$Z_W$ plane of the world coordinate system and a virtual viewpoint plane.

The second determination unit 23 calculates a vector $r_G$ from a corneal reflection point G to the pupil center P in the image plane $S_G$, and converts the vector $r_G$ into a vector r actually calculated by using a magnification ratio of the camera obtained from the distance OP. In this case, it is assumed that, considering each camera 10 as a pinhole model, the corneal reflection point G and the pupil center P are placed on a plane parallel to the virtual viewpoint plane X'-Y'. That is, the second determination unit 23 calculates relative coordinates of the pupil center P and the corneal reflection point G as the vector r on the plane parallel to the virtual viewpoint plane and including three-dimensional coordinates of the pupil P, and the vector r represents the actual distance from the corneal reflection point G to the pupil center P.

Subsequently, the second determination unit 23 assumes that, with respect to a gaze point T on the virtual viewpoint plane of a subject A, a gradient ϕ with respect to a horizontal axis X' of a straight line OT is equal to a gradient ϕ' with respect to a horizontal axis $X_G$ of the image plane of the vector r. Also, the second determination unit 23 calculates an angle θ between, a viewpoint vector of the subject A, that is, a vector PT connecting the pupil center P and the gaze point T and the reference line OP, by the following Formula (1) using parameters including a gain value k.

$$\theta = f_1(r) = k \times |r| \tag{1}$$

The calculation of the angles ϕ and θ is performed on the assumption that when the vector r on a plane on which the pupil center P exists is expanded onto the virtual viewpoint plane, it corresponds to a gaze point of a subject A. More specifically, it is assumed that the angle θ with respect to the reference line OP of the gaze PT of the subject A has a linear relationship to a distance |r| between the pupil center and the corneal reflection.

By using assumption that the angle θ and the distance |r| are obtained by linear approximation and the two gradients ϕ and ϕ' are identical to each other, (θ, ϕ) and (|r|, ϕ') can correspond in an one-to-one relationship. In this case, the second determination unit 23 obtains a vector OT connecting an origin point O set at a center of the aperture 12 of the camera 10 and a gaze point T on the virtual viewpoint plane by the following Formula (2). The vector OP can be obtained from the camera 10.

[Math. 1]

$$OT = \begin{pmatrix} |OP| \tan\theta \cos\phi \\ |OP| \tan\theta \sin\phi \\ 0 \end{pmatrix} \tag{2}$$

Finally, the second determination unit 23 obtains the gaze point Q that is an intersection point between the gaze vector PT and a plane subjected to viewing (display device 30) by the following Formula (3).

$$Q = nPT + P \tag{3}$$

However, there is, in general, a difference between a visual axis (axis passing through a pupil center and a central fovea) and an optical axis (normal line extending from a pupil to a center of a lens), and corneal reflection and the pupil center do not match each other even when the subject A gazes on the camera. Therefore, when an origin correction vector calibrating this is defined as $r_0$ and corneal reflection actually measured from the camera image—pupil center vector is defined as r', the vector r is expressed by $r = r' - r_0$, and therefore, Formula (1) is rewritten as the following Formula (4).

$$\theta = k \times |r' - r_0| \tag{4}$$

By performing origin correction on the measured r', it is possible to allow (θ, ϕ) and (|r|, ϕ') to correspond in a one-to-one relationship, and achieve high precise gaze point detection.

The calculation of the angles ϕ and θ is performed on the assumption that when the vector r ($=r' - r_0$) on a plane on which the pupil center P exists is expanded onto the virtual viewpoint plane, it corresponds to a gaze point of a subject A. More specifically, it is assumed that there is a linear relationship between the angle θ with respect to the reference line OP of the gaze PT of the subject A and a corrected value |r'−r$_0$| of a distance between the pupil center and the corneal reflection. Also, since, in the origin correction vector r$_0$ included in the function f$_1$, an actual vector between the corneal reflection and the pupil center when the subject A gazes on the camera (θ=0) is not zero, the vector r$_0$ is set as the vector between the corneal reflection and the pupil center. In this case, since the gain value k and the origin correction vector r$_0$ are different depending on subjects A or left and right eyeballs, calibration is needed. Therefore, as the gain value k and the origin correction vector r$_0$, values are used, which are obtained by correcting previously-set initial values by parameter correction processing to be described below. The distance between the pupil center and corneal sphere center and the visual axis (reference value) are required at the time of one-point calibration of the gaze point detection.

Figure 14:
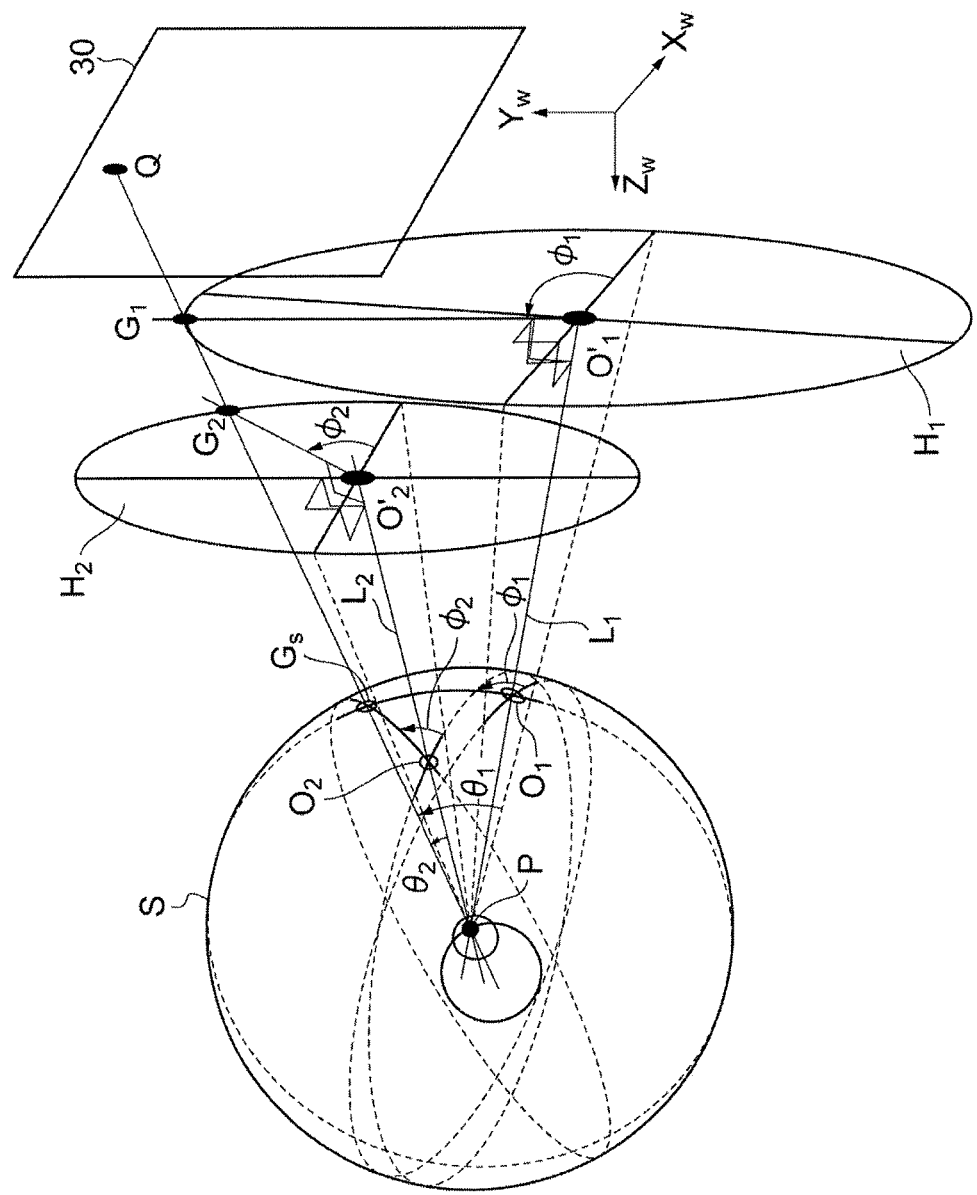
FIG. 14 is a diagram for describing a mechanism of gaze point detection.

Also, the second determination unit 23 detects a gaze point of the subject A on the screen of the display device 30 by referring to ϕ$_1$, ϕ$_2$, θ$_1$, and θ$_2$ that are the angles ϕ and θ calculated corresponding to the images of the two cameras 10. In this case, in order to describe mechanism of gaze point detection, a coordinate system as illustrated in FIG. 14 is defined. There are defined two virtual viewpoint planes H$_1$ and H$_2$ having origin points O$_1$' and O$_2$' corresponding to the positions of the two stereo cameras 10 and a virtual viewpoint spherical surface having an optional radius and a center that is the pupil center P. The two virtual viewpoint planes H$_1$ and H$_2$ are planes perpendicular to straight lines PO$_1$' and PO$_2$', respectively. Also, an intersection point between a straight line passing through the pupil center P and the gaze point Q on the display screen (gaze) and the virtual viewpoint spherical surface S is defined as G$_s$, an intersection point between a straight line passing through the pupil center P and the origin point O$_1$' and the virtual viewpoint spherical surface S is defined as O$_1$, and an intersection point between a straight line passing through the pupil center P and the origin point O$_2$' and the virtual viewpoint spherical surface S is defined as O$_2$. When an intersection point between the gaze PQ and the virtual viewpoint plane H$_1$ is defined as G$_1$, an angle between a straight line O$_1$'G$_1$ and a horizontal axis of the virtual viewpoint plane H$_1$ is ϕ$_1$. Similarly, when an intersection point between the gaze PQ and the virtual viewpoint plane H$_2$ is defined as G$_2$, an angle between a straight line O$_2$'G$_2$ and a horizontal axis of the virtual viewpoint plane H$_2$ is ϕ$_2$. In addition, an angle between an intersection line (curve) between a horizontal plane passing through a point O$_1$ and the spherical surface S and a curve O$_1$G$_5$, at the point O$_1$ on the virtual viewpoint spherical surface S is equal to the angle ϕ$_1$. Similarly, an angle between an intersection line (curve) between a horizontal plane passing through a point O$_2$ and the virtual viewpoint spherical surface S and a curve O$_2$G$_5$, at the point O$_2$ on the virtual viewpoint spherical surface S is equal to the angle ϕ$_2$. As described above, since the points P, O$_1$, and O$_1$' exist on the same straight line L$_1$ and the points P, O$_2$, and O$_2$' exist on the same straight line L$_2$, an angle between the straight line L$_1$ and the gaze is θ$_1$ and an angle between the straight line L$_1$ and the gaze is θ$_2$.

The second determination unit 23 can calculate a gaze point on the screen by referring to coordinates of positions of origin points O$_1$' and O$_2$' previously known, and the position and direction data of the display device 30 by using the above-described relationship. That is, it is possible to obtain relative position relationship of points G$_S$, O$_1$, and O$_2$ on the virtual viewpoint spherical surface S, from the angles ϕ$_1$, ϕ$_2$, θ$_1$, and θ$_2$ calculated by camera images of the two cameras 10. Therefore, the second determination unit 23 can uniquely obtain the gaze PG$_S$ from the coordinates of the origin points O$_1$' and O$_2$' previously known and the coordinates of the pupil center P previously calculated, and detect a gaze point Q by calculating an intersection point between the gaze PG$_S$ and the screen of the display device 30. Even when the gaze PG$_S$ obtained from the angles the angles ϕ$_1$ and θ$_1$ is misaligned with the gaze PG$_S$ obtained from the angles the angles ϕ$_2$ and θ$_2$, what is obtained by averaging them can be calculated as a final gaze vector.

Here, a function f$_1$ used to calculate the gaze by the second determination unit 23 includes a gain value k and an origin correction vector r$_0$ as parameters. The gain value k is, as seen from Formula (4), a scale factor used in the case of obtaining the angle θ from the vector r, on the assumption that the magnitude of the vector r=r'−r$_0$ after a corneal reflection—pupil center vector r' is adjusted and the angle θ representing the gaze are in a linear relationship. Ideally, in a case in which the angle θ and the vector |r'| are in a linear relationship, when the gain value k is obtained, it is possible to calculate the angle θ. In other words, when the angle θ is zero (θ=0), that is, the subject A gases on the camera, the vector |r'| is zero (|r'|=0). However, in practice, the virtual axis (gaze) of an eyeball and an optical axis does not match each other, and when the angle θ is zero (θ=0), the vector |r'| is not zero (|r'|≠0). Also, in a case in which the subject A is changed, the vector |r| when the angle θ is zero is different. Also, the visual axis of the eyeball is a straight line connecting the central fovea of the eyeball of the subject and the gaze point of the subject.

Next, a method of obtaining k and the vector r$_0$ will be described. By Formula (4), the vectors θ$_1$ and θ$_2$ can be expressed by the following Formulas (5) and (6) respectively.

$$\theta_1 = kr_1 = k \times (r'_1 - r_0) \quad (5)$$

$$\theta_2 = kr_2 = k \times (r'_2 - r_0) \quad (6)$$

Since, in the above Formulas, the origin correction vector r$_0$ is uniquely determined for respective eyeballs, r$_0$ is resulted regardless of the camera. The interval between the two cameras is expressed by an angle and defined by the following Formula (7).

[Math. 2]

$$|\theta_1 - \theta_2| = |\overrightarrow{O_1 O_2}| = \angle O_1 P O_2 \quad (7)$$

The following Formula (8) is obtained from Formulas (5) to (7), and a coefficient k (calibration value) is calculated from the Formula (8).

[Math. 3]

$$k = \frac{|\theta_2 - \theta_1|}{|r'_2 - r'_1|} = \frac{|\overrightarrow{O_1 O_2}|}{|r'_2 - r'_1|} = \frac{\angle O_1 P O_2}{|r'_2 - r'_1|} \quad (8)$$

Since the positions of the two cameras are known, ∠O$_1$PO$_2$ is always known. Therefore, although the subject does not gaze on a specific position, the coefficient k can be calculated from the vector r' actually measured by each camera.

Also, the second determination unit 23 calculates an origin correction vector r$_0$ by the one-point calibration method. A method of calculating the origin correction vector $r_0$ by the one-point calibration method will be described below in detail. First, the second determination unit 23 displays a visual mark (specified point) at an arbitrary position on the display screen of the display device 30 and allows the subject A to gaze on the visual mark. In this state, the second determination unit 23 detects a gaze point on a projected virtual viewpoint plane. Next, the second determination unit 23 calculates, as a calibration quantity, a difference between the detected gaze point and a point obtained by projecting coordinates of the visual mark onto the projected virtual viewpoint plane. Then, the second determination unit 23 determines the origin correction vector $r_0$ based on the calibration quantity. In this way, the second determination unit 23 performs high accuracy gaze point detection according to Formula (4).

By detecting the gaze point, the second determination unit 23 can detect a gaze of the subject A. The second determination unit 23 may output a result of the detection at the timing when the gaze of the subject A is detected. In this case, the second determination unit 23 also functions as a gaze detection unit and the pupil detection system 1 functions as a gaze detection system.

Figure 15:
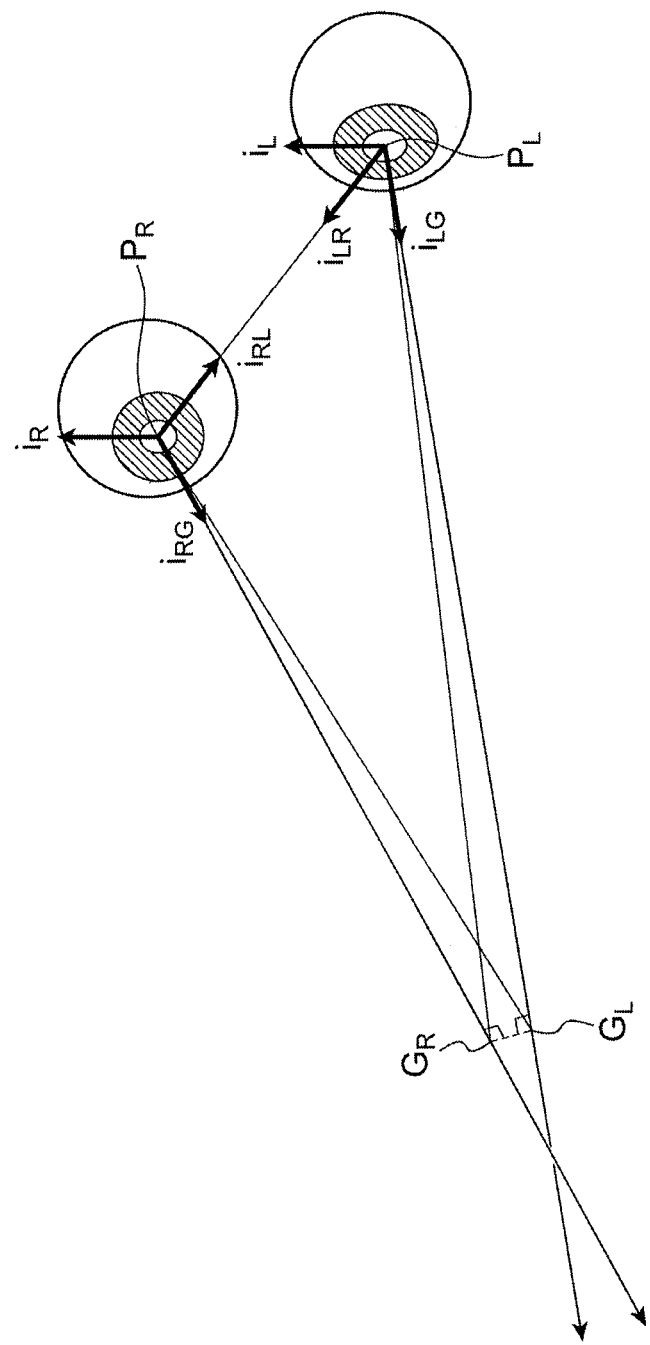
FIG. 15 is a diagram for describing gaze difference.

When a human gazes on one point by two eyes, it is ideal that the gazes of the two eyes are superimposed on the one point. In this case, a plane is configured by three points of an intersection point of the left gaze and the right gaze, the pupil center of the right eye (right pupil center), and the pupil center of the left eye (left pupil center). By using the above property, the second determination unit 23 may determine whether the left and right gazes are correctly detected, and whether the coordinates of the pupil center that is presumption thereof are correct. However, since, in reality, the two gazes of a human may be slightly different and an error of the device may occur, the two gazes are generally shifted along the height direction of the subject A, as shown in FIG. 15. The right pupil center and the left pupil center are respectively defined as $P_R$ and $P_L$, unit direction vectors of the gazes extending from the right eye and the left eye are respectively defined as $i_{RG}$ and $i_{LG}$. Also, a unit direction vector extending from the right pupil center to the left pupil center is defined as $i_{RL}$, and a unit direction vector extending from the left pupil center to the right pupil center is defined as $i_{LR}$. Also, points on the gazes when the two gazes are closest to each other are respectively defined as $G_R$ and $G_L$. In this case, a normal-line unit vector $i_R$ of a plane passing through three points $P_R$, $P_L$, and $G_R$ is expressed by the following Formula (9) representing a cross product.

$$i_R = i_{RG} \times i_{RL} \quad (9)$$

Similarly, a normal-line unit vector unit vector $i_L$ of a plane passing through three points $P_R$, $P_L$, and $G_L$ is expressed by the following Formula (10).

$$i_L = i_{LG} \times i_{LR} \quad (10)$$

When the gazes of the two eyes intersects each other, the two normal-line unit vectors $i_R$ and $i_L$ are identical to each other, and therefore, an angle $\delta$ obtained by the following Formula (11) becomes zero.

[Math. 4]

$$\delta = \cos^{-1} \frac{i_R \cdot i_L}{|i_R| \cdot |i_L|} \quad (11)$$

By using the principle, when an angel $\delta$ between the two normal-line unit vectors $i_R$ and $i_L$ is within a predetermined range ($|\delta| \leq \delta_0$ when a threshold is defined as $\delta_0$), the second determination unit 23 determines that the left and right gazes are correct, and selects a combination of left and right pupil positions corresponding to the gazes. On the other hand, when the angel $\delta$ exceeds the threshold $\delta_0$, the second determination unit 23 determines that the left and right gazes are incorrect, and excludes a combination of left and right pupil positions corresponding to the gazes. $|\delta| \leq \delta_0$ means that a difference between the left gaze and the right gaze in the height direction of the subject is equal to or less than the threshold.

The second determination unit 23 performs the above processing on all combination of left pupil candidates and right pupil candidates and selects a combination of the left and right pupil positions predicted as being correct. This processing means determining that the left pupil and the right pupil are respectively located at the left pupil center and the right pupil center corresponding to the left gaze and the right gaze determined as being correct. The second determination unit may output only the left gaze and the right gaze determined as being correct as a result of final determination, not outputs a result of determination of pupil positions. Even in this case, the second determination unit 23 functions also as a gaze detection unit and the pupil detection system 1 functions as a gaze detection system.

Also, when the gaze points on the display device 30 are detected, the second determination unit 23 may determine whether the gaze (and the pupil position) is correct based on a distance between the right and left gaze points. Specifically, the second determination unit 23 obtains intersection points between the left and right gazes obtained before calculation of the angle $\delta$ and the screen plane as the gaze points, and obtains a distance between the gaze point of the right eye and the gaze point of the left eye by round-robin. Then, when the distance is equal to or less than a predetermined threshold, the second determination unit 23 determines that the left and right gazes are correct.

[Pupil Detection Program]

Figure 16:
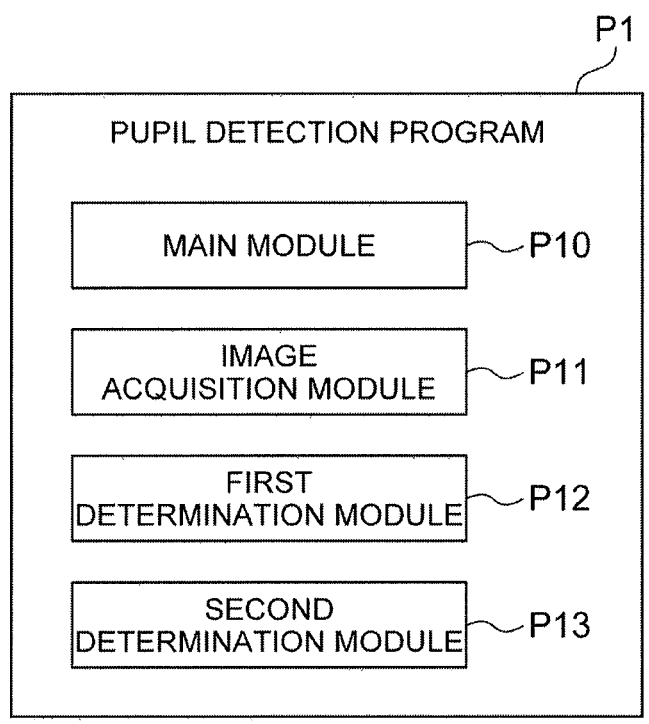
FIG. 16 is a diagram illustrating a configuration of a pupil detection program according to an embodiment.

Subsequently, a pupil detection program P1 for implementing the image processing device 20 will be described with reference to FIG. 16.

The pupil detection program P1 includes a main module P10, an image acquisition module P11, a first determination module P12, and a second determination module P13.

The main module P10 is a part for controlling a pupil detection function comprehensively. Functions realized by performing the image acquisition module P11, the first determination module P12, and the second determination module P13 are identical to those of the image acquisition unit 21, the first determination unit 22, and the second determination unit 23.

The pupil detection program P1 may be provided in the form of being recorded fixedly on recording media such as CD-ROM, DVD ROM, semiconductor memory, and the like. The pupil detection program P1 may also be provided through a communication network as data signals superimposed on a carrier.

As described above, a pupil detection system according to one aspect of the present invention includes a vector calculation unit configured to calculate a plurality of candidate vectors each connecting a corneal sphere center and a pupil center by a stereo method based on a first pupil image of a subject which is picked up by a first camera and a second pupil image of the subject which is picked up by a second camera, the corneal sphere center being an intersection point between an axis passing through the first camera and a corneal reflection point obtained from the first pupil image and an axis passing through the second camera and a corneal reflection point obtained from the second pupil image; and a determination unit configured to select, from among the plurality of candidate vectors, a candidate vector satisfying a vector condition in which an angle between the pupil center and a reference line, which is set based on a position of at least one of the first camera and the second camera, is equal to or less than a predetermined threshold and determine that a pupil is located at a pupil center corresponding to the selected candidate vector.

A pupil detection method according to one aspect of the present invention is the pupil detection method to be performed by a pupil detection system including a processor, and includes a vector calculation step of calculating a plurality of candidate vectors each connecting a corneal sphere center and a pupil center by a stereo method based on a first pupil image of a subject which is picked up by a first camera and a second pupil image of the subject which is picked up by a second camera, the corneal sphere center being an intersection point between an axis passing through the first camera and a corneal reflection point obtained from the first pupil image and an axis passing through the second camera and a corneal reflection point obtained from the second pupil image; and a determination step of selecting, from among the plurality of candidate vectors, a candidate vector satisfying a vector condition in which an angle between the pupil center and a reference line, which is set based on a position of at least one of the first camera and the second camera, is equal to or less than a predetermined threshold and determining that a pupil is located at a pupil center corresponding to the selected candidate vector.

A pupil detection program according to one aspect of the present invention causes a computer to function as: a vector calculation unit configured to calculate a plurality of candidate vectors each connecting a corneal sphere center and a pupil center by a stereo method based on a first pupil image of a subject which is picked up by a first camera and a second pupil image of the subject which is picked up by a second camera, the corneal sphere center being an intersection point between an axis passing through the first camera and a corneal reflection point obtained from the first pupil image and an axis passing through the second camera and a corneal reflection point obtained from the second pupil image; and a determination unit configured to select, from among the plurality of candidate vectors, a candidate vector satisfying a vector condition in which an angle between the pupil center and a reference line, which is set based on a position of at least one of the first camera and the second camera, is equal to or less than a predetermined threshold and determine that a pupil is located at a pupil center corresponding to the selected candidate vector.

According to the aspect, the plurality of candidate vectors each connecting the corneal sphere center and the pupil center are calculated, among them, a candidate vector of which the direction is regarded as being correct is selected, and it is determined that a pupil is located at the pupil center corresponding to the selected vector. As described above, by checking the direction with respect to each of the plurality of candidate vectors, it is possible to correctly detect the pupil even when a noise is included in a pupil image.

The effects will be further described. When a plurality of corneal reflection points are detected in at least one of the first pupil image and the second pupil image, that is, when a noise occurs in the pupil image, first, a plurality of candidate vectors are obtained by combining corneal reflection points in both the images by round-robin, and only candidate vectors satisfying the vector condition are selected by checking the direction and length of each candidate vector. This selection means excluding candidate vectors not satisfying the vector condition, thus reducing erroneous detection of the pupil position. That is, it is possible to correctly detect a pupil.

Furthermore, according to the above aspect, it is possible to discriminate corneal reflection due to a light source provided in the camera from corneal reflection due to a light source spaced apart from the camera.

In the pupil detection system according to another aspect, the determination unit may select candidate vectors satisfying a vector condition in which an angle with respect to the reference line is equal to or less than the predetermined threshold and the length is within the predetermined range.

As described above, by checking both the direction and the length of each of the plurality of candidate vectors, it is possible to detect a pupil more precisely even when a noise is included in the pupil image.

In the pupil detection system according to another aspect, the vector calculation unit may perform processing of calculating a pupil center by using corneal reflection candidate points before calculation of the candidate vectors, and when it has failed to calculate the pupil center by using the corneal reflection candidate points, exclude relevant corneal reflection candidate points, and calculate only candidate vectors corresponding to the corneal reflection candidate points that were not excluded.

In this case, since the relevant corneal reflection candidate points by using which it has failed to calculate the pupil center (that is, corneal reflection candidate points regarded as being incorrect) are excluded before the candidate vectors are obtained, candidate vectors predicted as certainly being incorrect are not calculated. The above processing reduces the number of candidate vectors, thus reducing time taken to detect a pupil accordingly.

In the pupil detection system according to another aspect, the vector calculation unit may calculate a plurality of candidate vectors with respect to each of the left pupil and the right pupil of a subject, and the determination unit may determine the left pupil center and the right pupil center by selecting the candidate vectors satisfying the vector condition, with respect to each of the left pupil and the right pupil of a subject, respectively calculate the left gaze and the right gaze based on the left pupil center and the right pupil center, and determine that the left gaze and the right gaze are correct gazes in a case where an angle between a normal line of a plane defined by the left pupil center, the right pupil center, and the left gaze and a normal line of a plane defined by the left pupil center, the right pupil center, and the right gaze satisfies the gaze condition in which the angle is within the predetermined range.

The angle between the two normal lines corresponds to a difference between the left and right gazes in the height direction of the subject. By checking the difference, it is possible to correctly detect a gaze even when a noise is included in the pupil image.

In the pupil detection system according to another aspect, the determination unit may determine that the left pupil and the right pupil are respectively located at the left pupil center and the right pupil center corresponding to the left gaze and the right gaze determined as being correct.

In this case, it is possible to correctly detect a pupil in consideration also of correctness of the gaze.

The gaze detection system according to one aspect of the present invention includes a gaze detection unit that detects a gaze of a subject based on the pupil center determined by the pupil detection system.

According to the above aspect, since the gaze of the subject is detected based on the pupil center corresponding to the candidate vectors regarded as being correct, it is possible to correctly specify the gaze even when a noise is included in the pupil image.

Until now, the present invention have been described in detail referring to the embodiments thereof. However, the present invention is not limited to the embodiments. While the invention has been described in detail and with reference to specific embodiments thereof, it will be apparent to one skilled in the art that various changes and modifications can be made therein without departing from the spirit and scope thereof.

When candidates of left and right pupil positions are obtained, the first determination unit 22 may select only left and right pupil positions in which a distance between pupil centers (distance between pupils) is within a predetermined range. This processing may be performed before or after determination of the vector condition is performed.

Specifically, the first determination unit 22 selects one of candidates of the extracted left pupil center and one of candidates of the right pupil center, and calculates a distance between the two selected pupil centers (distance between pupils). The distance between pupils I is expressed by the following Formula (12). Here, $P_1$ and $P_2$ are three-dimensional coordinates of the left and right pupil centers.

$$I=|P_1-P_2| \quad (12)$$

Then, the first determination unit 22 selects a pair of pupil centers satisfying the distance condition in which the distance between pupils is within the predetermined range and excludes a pair not satisfying the distance condition. The first determination unit 22 performs processing on all combinations of the left pupil center and the right pupil center.

Generally, an inter-pupil distance of a human being is about 65 mm. Therefore, considering a change in the distance between pupils due to individual differences and congestion or the like, a range set in order for the distance condition may be a range including 65 mm. For example, the lower limit of the range may be 50 mm, 55 mm, or 60 mm and the upper limit of the range may be 70 mm, 75 mm, or 80 mm.

That is, in the pupil detection system according to another aspect, the vector calculation unit may calculate a plurality of candidate vectors with respect to each of the left pupil and the right pupil of a subject, and the determination unit may determine the left pupil center and the right pupil center with respect to each of the left pupil and the right pupil and also determine that the left pupil and the right pupil are respectively disposed at the left pupil center and the right pupil center satisfying the distance condition in which the distance between pupils is within the predetermined range, corresponding to candidate vectors satisfying the vector condition and also based on the left pupil center and the right pupil center.

As described above, by checking also an inter-pupil distance, it is possible to correctly detect a pupil even when the pupil image includes a noise.

The determination using a distance condition may be performed based on a distance between cornea centers (distance between corneas), rather than the distance between pupils.

The first determination unit 22 may perform the determination using the vector condition with respect to a visual axis obtained from the pupil centers.

The pupil detection system may include three or more cameras.

For example, three cameras may be disposed at positions of vertexes of a regular triangle on the virtual viewpoint plane or four cameras may be disposed at positions of four vertexes of a square on the virtual viewpoint plane. In this case, it is possible to obtain the pupil position and the gaze according to the aforementioned embodiment by using images picked up by two cameras that have been able to capture pupil or corneal reflection, thus obtaining a pupil or a gaze more certainly.

Although the pupil detection system 1 includes the second determination unit 23 in the aforementioned embodiment, the second determination unit 23 may be omitted. That is, the pupil detection system 1 may output the pupil position satisfying the vector condition as a final determination result.

Although, in the aforementioned embodiment, the vector condition is defined as a "condition in which an angle between the candidate vector and a reference line is equal to or less than a predetermined threshold and a length of the candidate vector is within a predetermined range," there may be no need to consider the length of the candidate vector. That is, the vector condition may be defined as a "condition in which an angle between the candidate vector and a reference line is equal to or less than a predetermined threshold". This means that the vector condition (1) of the aforementioned embodiment is only used.

Although the first determination unit 22 generates the difference image from the bright pupil image and the dark pupil image and calculates pupil coordinates from the difference image in the aforementioned embodiment, the first determination unit 22 may obtain the pupil position and the corneal reflection position from one set of pupil coordinates (bright pupil image or the dark pupil image) input from the image acquisition unit 31, instead of generating of the difference image. Specifically, the first determination unit 22 performs binarization and labeling on the one sheet of pupil image and selects pupil candidates (or corneal reflection candidate points) from among connection components of a pixel assigned a label based on shape parameters such as a pupil (or corneal reflection point)-like area, size, area ratio, square degree, and feature amount. Then, the first determination unit 22 acquires a position of each pupil candidate (or each corneal reflection candidate point)

REFERENCE SIGNS LIST

1 pupil detection system
10 camera (first camera or second camera)
20 image processing device
21 image acquisition unit
22 first determination unit
23 second determination unit
P1 pupil detection program
P10 main module
P11 image acquisition module
P12 first determination module
P13 second determination module

The invention claimed is:

1. A pupil detection system comprising:
   a non-transitory computer-readable medium comprising at least one memory operable to store program instructions; and at least one processor operable to access the at least one memory and read and carry out the program instructions, the program instructions including:

vector calculation instructions to cause the at least one processor to calculate a plurality of candidate vectors by a stereo method based on a first pupil image of a subject which is picked up by a first camera and a second pupil image of the subject which is picked up by a second camera, each of the plurality of candidate vectors connecting a corneal sphere center and a pupil center, the corneal sphere center being an intersection point between an axis passing through the first camera and a corneal reflection point obtained from the first pupil image and an axis passing through the second camera and a corneal reflection point obtained from the second pupil image; and determination instructions to cause the at least one processor to select, from among the plurality of candidate vectors, a candidate vector satisfying a vector condition in which an angle between the candidate vector and a reference line, which is set based on the pupil center and a lens center of at least one of the first camera and the second camera, is equal to or less than a predetermined threshold, and determine that the pupil is located at the pupil center corresponding to the candidate vector that is selected from the plurality of candidate vectors.

2. The pupil detection system according to claim 1, wherein the determination instructions are further configured to cause at least one processor to select a candidate vector satisfying a vector condition in which the angle by the reference line is equal to or less than the predetermined threshold and a length is within a predetermined range.

3. The pupil detection system according to claim 1,
wherein the vector calculation instructions are further configured to cause at least one processor to:
perform processing of calculating the pupil center using corneal reflection candidate points before calculation of the candidate vectors,
exclude, in response to a failure to calculate a pupil center using the corneal reflection candidate point, the corneal reflection candidate point, and
calculate only a candidate vector corresponding to the corneal reflection candidate point that was not excluded.

4. The pupil detection system according to claim 1,
wherein the vector calculation instructions are further configured to cause at least one processor to calculate a plurality of candidate vectors with respect to each of a left pupil and a right pupil of the subject, and
the determination instructions are further configured to cause at least one processor to:
determine a left pupil center and a right pupil center with respect to the left pupil and the right pupil, respectively, and
determine whether the left pupil and the right pupil are respectively at the left pupil center and the right pupil center which correspond to the candidate vectors satisfying the vector condition and satisfy a distance condition in which an inter-pupil distance based on the left pupil center and the right pupil center is within a predetermined range.

5. The pupil detection system according to claim 1,
wherein the vector calculation instructions are further configured to cause at least one processor to calculate a plurality of candidate vectors with respect to each of a left pupil and a right pupil of the subject, and the determination instructions are further configured to cause at least one processor to:
determine a left pupil center and a right pupil center by selecting candidate vectors satisfying the vector condition with respect to each of the left pupil and the right pupil,
calculate a left gaze and a right gaze based on the left pupil center and the right pupil center, respectively, and
determine that the left gaze and the right gaze are correct when an angle between a normal line of a plane defined by the left pupil center, the right pupil center, and the left gaze and a normal line of a plane defined by the left pupil center, the right pupil center, and the right gaze satisfies a gaze condition in which the angle is equal to or less than a predetermined threshold.

6. The pupil detection system according to claim 5, wherein the determination instructions are further configured to cause at least one processor to determine that the left pupil and the right pupil are located at the left pupil center and the right pupil center corresponding to the left gaze and the right gaze determined as being correct, respectively.

7. A gaze detection system comprising:
a non-transitory computer-readable medium comprising at least one memory operable to store program instructions; and
at least one processor operable to access the at least one memory and read and carry out the program instructions, the program instructions including gaze detection instructions configured to cause at least one processor to detect a gaze of the subject based on the pupil center determined by the pupil detection system according to claim 1.

8. A gaze detection system comprising:
a non-transitory computer-readable medium comprising at least one memory operable to store program instructions; and
at least one processor operable to access the at least one memory and read and carry out the program instructions, the program instructions including gaze detection instructions configured to cause at least one processor to detect a left gaze and a right gaze of the subject based on the left pupil center and the right pupil center determined by the pupil detection system according to claim 4.

9. A pupil detection method, which is performed by a pupil detection system including a non-transitory computer-readable medium comprising at least one memory operable to store program instructions; and
at least one processor operable to access the at least one memory and read and carry out the program instructions, the program instructions including:
a processor, the pupil detection method comprising:
calculating a plurality of candidate vectors by a stereo method based on a first pupil image of a subject which is picked up by a first camera and a second pupil image of the subject which is picked up by a second camera, each of the plurality of candidate vectors connecting a corneal sphere center and a pupil center, the corneal sphere center being an intersection point between an axis passing through the first camera and a corneal reflection point obtained from the first pupil image and an axis passing through the second camera and a corneal reflection point obtained from the second pupil image; and
selecting, from among the plurality of candidate vectors, a candidate vector satisfying a vector condition in which an angle between the candidate vector and a reference line, which is set based on the pupil center and a lens center of at least one of the first camera and the second camera, is equal to or less than a predetermined threshold, and determining that the pupil is located at the pupil center corresponding to the candidate vector that is selected from the plurality of candidate vectors.

10. A pupil detection program, stored on a non-transitory computer readable medium, causing a computer to:

calculate a plurality of candidate vectors by a stereo method based on a first pupil image of a subject which is picked up by a first camera and a second pupil image of the subject which is picked up by a second camera, each of the plurality of candidate vectors connecting a corneal sphere center and a pupil center, the corneal sphere center being an intersection point between an axis passing through the first camera and a corneal reflection point obtained from the first pupil image and an axis passing through the second camera and a corneal reflection point obtained from the second pupil image; and select, from among the plurality of candidate vectors, a candidate vector satisfying a vector condition in which an angle between the candidate vector and a reference line, which is set based on the pupil center and a lens center of at least one of the first camera and the second camera, is equal to or less than a predetermined threshold, and determine that the pupil is located at the pupil center corresponding to the candidate vector that is selected from the plurality of candidate vectors.

* * * * *